United States Patent [19]

Lang et al.

[11] 4,151,162

[45] Apr. 24, 1979

[54] DIAZOMEROCYANINES AND MESOMERIC FORMS THEREOF

[75] Inventors: Gerard Lang, Epinay-sur-Seine; Andrée Bugaut, Boulogne-sur-Seine, both of France

[73] Assignee: L'Oreal, Paris, France

[21] Appl. No.: 707,769

[22] Filed: Jul. 22, 1976

Related U.S. Application Data

[60] Division of Ser. No. 554,701, Mar. 3, 1975, Pat. No. 3,986,499, which is a continuation-in-part of Ser. No. 259,689, Jun. 5, 1972, Pat. No. 3,869,544.

[30] Foreign Application Priority Data

Jun. 4, 1971 [LU] Luxembourg ............................. 63287
Jan. 6, 1972 [LU] Luxembourg ............................. 64565
Aug. 30, 1974 [LU] Luxembourg ............................. 70835

[51] Int. Cl.² .................. A61K 7/13; C09B 29/06; C09B 29/08

[52] U.S. Cl. .................. 260/158; 544/105; 544/330; 544/332; 544/292; 8/10; 8/10.1; 8/10.2; 8/11; 260/154; 260/156; 260/157; 260/162; 260/163; 260/326.62; 260/305; 260/306.7 T; 260/307 D; 260/307 F; 260/306.8 R; 260/306.8 A; 260/306.8 D; 260/326.47; 260/326.47; 260/326.5 L; 260/326.15; 260/326.14 R; 260/326.9; 546/306; 546/289; 546/162; 548/306; 548/315

[58] Field of Search .......... 260/244 R, 294.9, 293.55, 260/293.62, 305, 306.7 T, 306.8 R, 306.8 D, 306.8 A, 307 R, 307 D, 309, 309.2, 309.6, 309.7, 310 R, 310 C, 154, 156, 157, 158, 162, 163, 165

[56] References Cited

U.S. PATENT DOCUMENTS

| | | | |
|---|---|---|---|
| 2,951,847 | 9/1960 | Baumann et al. | 260/305 |
| 3,043,828 | 7/1962 | Huenig | 260/305 X |
| 3,499,902 | 3/1970 | Coles et al. | 260/305 X |
| 3,717,629 | 2/1973 | Maier et al. | 260/244 R |
| 3,749,716 | 7/1973 | Kalopissis | 260/244 R |
| 3,869,454 | 3/1975 | Lang et al. | 260/244 R |

Primary Examiner—Floyd D. Higel
Attorney, Agent, or Firm—Cushman, Darby & Cushman

[57] ABSTRACT

Dyes for application to hair to impart rich color nuances thereto, include diazamerocyanines, the mesomeric forms thereof and the salts thereof, of the formula

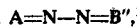

wherein A is

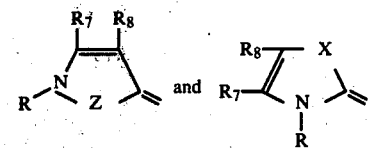

and wherein B" is

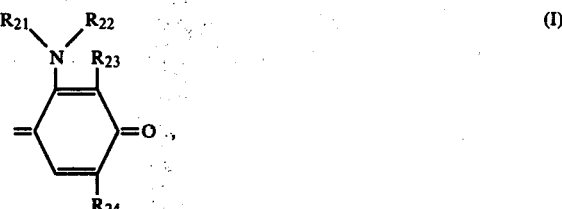

(I)

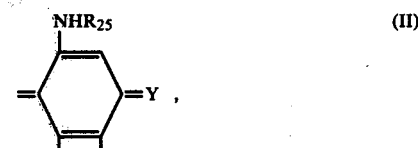

(II)

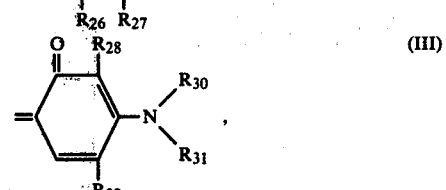

(III)

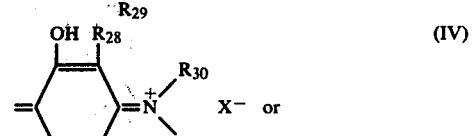

(IV)

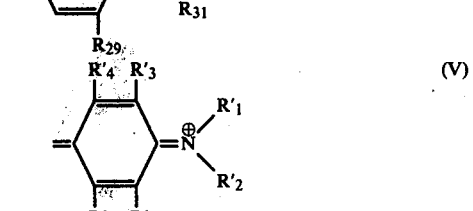

(V)

3 Claims, No Drawings

DIAZOMEROCYANINES AND MESOMERIC FORMS THEREOF

CROSS-REFERENCE TO RELATED APPLICATIONS

This is a Rule 60 division of U.S. application Ser. No. 554,701, filed Mar. 3, 1975 and now U.S. Pat. No. 3,986,499 which is in turn a continuation-in-part application of U.S. application Ser. No. 259,689, filed June 5, 1972, now U.S. Pat. No. 3,869,454.

Currently, one of the most frequently used processes in capillary dyeing includes using oxidation dyes or "bases" associated with dyeing modifiers or "couplers" which can be aromatic metadiamines or metaaminophenols, or pyrazolones or diketones. When using this process of capillary dyeing, an oxidizing agent such as hydrogen peroxide in alkaline media is added to the mixture of bases and couplers selected.

It is known to use heterocyclic hydrazones admixed with couplers for dyeing hair, as described for example in French Pat. No. 1,599,968.

However, this process has the disadvantage of requiring the use of hydrogen peroxide in an alkaline medium, which has been found to cause degradation of the hair, which rapidly becomes porous and brittle. Further, the shades obtained are reproducible only with great difficulty because of secondary reactions that occur along with the desired reaction between hydrazone and coupler. An additional disadvantage is that the hydrazones are relatively irritating to the skin, which often causes problems in use.

The present invention makes it possible to avoid these drawbacks by using, not a mixture of hydrazone and couplers thereof, but their coupling products, which constitute direct dyes which can be used over a varied range of pH and are capable of forming easily reproducible shades. One embodiment of the present invention has as its object novel dyeing compositions for human hair, characterized by the fact that they contain in solution at least a diazamerocyanine or a diazamerocyanine salt of the formula

wherein A is a nitrogen heterocycle of the formula

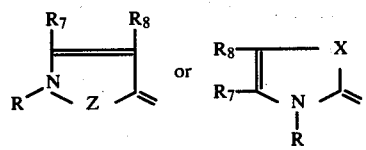

wherein R is selected from the group consisting of lower alkyl having 1–4 carbon atoms and phenyl; X is selected from the group consisting of oxygen, sulfur, —NR'—, wherein R' is lower alkyl having 1–4 carbon atoms,

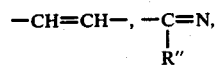

wherein R" is selected from the group consisting of hydrogen and lower alkyl having 1–4 carbon atoms, and —C(R")(R")—, wherein R" each independently have the meaning given above, Z is a member selected from the group consisting of —CH=CH— and —NR'"—, wherein R'" is a lower alkyl having 1–4 carbon atoms; $R_7$ is selected from the group consisting of hydrogen, lower alkyl having 1–4 carbon atoms and phenyl; $R_8$ is selected from the group consisting of hydrogen and lower alkyl having 1–4 carbon atoms, provided that when $R_7$ and $R_8$, taken together with the carbon atoms to which they are linked, form a benzene ring, a halogen-substituted benzene ring, a benzene ring substituted with lower alkyl having 1–4 carbon atoms, a benzene ring substituted with lower alkoxy having 1–4 carbon atoms or a nitro-substituted benzene ring: B is selected from the group consisting of (i) a nitrogen-containing heterocycle different from the nitrogen containing heterocycle of A; (ii) a group of the formula

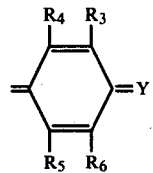

wherein Y is a member selected from the group consisting of oxygen and

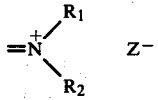

wherein $R_1$ and $R_2$ each independently represent a member selected from the group consisting of hydrogen, lower alkyl having 1–4 carbon atoms and phenyl; and $Z^-$ is an anion derived from a member selected from the group consisting of inorganic acids and organic acids, such as halide, fluoborate, perchlorate, sulfate, bisulfate and acetate; $R_3$ represents a member selected from the group consisting of hydrogen, lower alkyl, lower alkoxy and phenylcarbamyl; $R_4$ and $R_6$ each independently represent a member selected from the group consisting of hydrogen, lower alkyl having 1–4 carbon atoms and lower alkoxy having 1–4 carbon atoms, and $R_5$ represents a member selected from the group consisting of hydrogen, amino, alkylated amino having 1–4 carbon atoms, acylated amino having 2–5 carbon atoms; $R_5$ and $R_6$ being able, together with the carbon atoms to which they are attached, to form a condensed benzene rings; (iii) a cycle having the formula

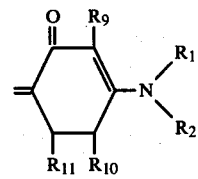

wherein $R_1$ and $R_9$, together with the nitrogen and carbon atoms to which they are attached, form a compound selected from the group consisting of a saturated heterocycle having 5 ring atoms, an unsaturated heterocycle having 5 ring atoms, a saturated heterocycle having 6 ring atoms, an unsaturated heterocycle having 6 ring atoms, in which case $R_{10}$ is hydrogen and $R_2$ represents a member selected from the group consisting of hydrogen and lower alkyl having 1–4 carbon atoms; or wherein $R_2$ and $R_{10}$, when taken together with the nitrogen and carbon atoms to which they are attached, form a compound selected from the group consisting of a saturated heterocycle having 5 ring atoms, an unsaturated heterocycle having 5 ring atoms, a saturated heterocycle having 6 ring atoms and an unsaturated heterocycle having 6 ring atoms, in which case $R_9$ is hydrogen and $R_1$ is selected from the group consisting of hydrogen, lower alkyl having 1–4 carbon atoms and acyl having 2 to 5 carbon atoms; and (iv) a cycle having the formula

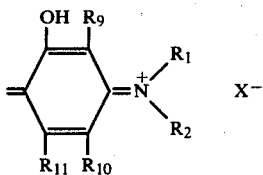

wherein $R_1$, $R_2$, $R_9$, $R_{10}$ and $R_{11}$ have the meaning given above and $X^-$ represents an anion derived from a member selected from the group consisting of inorganic acid and organic acid, such as halide, fluoborate, perchlorate, sulfate, bisulfate and acetate.

The organic or inorganic acid salts of the compounds of Formula I can be acetates, oxalates, hydrochlorides, hydrobromides, persulfates or perchlorates. Of course, other organic and inorganic salts may be used.

Amino groups are compounds having the formula:

where $R_a$ and $R_b$ are each independently hydrogen and lower alkyl having 1–4 carbon atoms.

The above-described hair dyeing compositions according to the present invention are aqueous solutions, to which have usually been added low molecular weight alcohols such as ethanol or isopropanol, or glycols such as propylene glycol or butylglycol, the alcohol or glycol facilitating the solution of the dye in the composition. These solutions are easily prepared by dissolving one or more compounds of Formula I in water or in a water-alcohol mixture. The proportion of alcohol used is generally between 20 and 70% by weight, while the proportion of glycol is generally between 1 and 6% by weight.

The concentration of the dye or dyes of Formula I in the dyeing compositions according to the present invention can vary over broad limits, because of the great affinity of these compounds for keratinous fibers. This concentration is generally between about 0.0001 and about 0.5% by weight and preferably between about 0.002 and about 2% by weight.

The pH of the compositions according to the present invention is generally between about 2.5 and 10 and preferably between about 3 and 8. Preferably, however, the pH is adjusted to the desired value by addition of an acid such as orthophosphoric acid, lactic acid or acetic acid or a base such as mono-, di- or triethanolamine or ammonia.

The compositions according to the present invention can contain one or more of the dyes of Formula I, to make it possible to obtain on the hair shades rich in glints that go from yellow to blue, covering the light spectrum. The compositions according to the invention can, however, contain other direct dyes, for example, azo or anthraquinone dyes, nitro dyes of the benzene series, indoanilines, indophenols or indamines.

The hair-dyeing compositions according to the present invention can also contain various adjuvants and ingredients customarily used in capillary cosmetics, for example, wetting agents, dispersing agents, swelling agents, penetrating agents, thickeners, softeners or perfumes. They can also be packaged under pressure in aerosol bombs or containers, together with a conventional aerosol propellant such as dichlorodifluoromethane, trichloromonofluoromethane and their mixtures. Of course, other conventional aerosol propellants can be used.

Dyeing of keratinous fibers, particularly human hair, with the dye compositions according to the invention, can be performed in the usual way, by application at ambient temperature of the composition to the fibers to be dyed, the composition being left in contact for a period varying from 3 to 30 minutes. Following this application, the fibers are rinsed and, if desired, washed. Thereafter the treated fibers are dryed.

In another embodiment of the present invention the compounds of Formula I can be employed in the production of capillary setting lotions. These lotions comprise an aqueous dilute alcohol solution, at least one cosmetic resin and at least a compound of Formula I or a salt thereof as defined above. The setting lotions according to the invention generally contain from 20 to 70% by weight of the total hair-setting lotion composition of a low molecular weight alkanol such as ethanol or isopropanol and from 1 to 3% by weight of cosmetic resin.

Representative cosmetic resins that can be employed in the hair-setting lotions of the present invention include, for instance, polyvinyl pyrrolidone having a molecular weight of 40,000–400,000, copolymers of crotonic acid and vinyl acetate, said copolymers having a molecular weight ranging from about 10,000 to 70,000, copolymers vinyl pyrrolidone and vinyl acetate, wherein the ratio of PVP to VA ranges between 50–70:50–30, said copolymer having a molecular weight ranging from about 30,000 to 200,000 and maleic anhydride-butylvinyl ether copolymers, a 1% solution of which in methylethyl ketone has a viscosity of 0.1–3.5 cps at 25° C. These resins are used in a proportion of 1 to 3% by weight of the hair-setting lotion composition.

The pH of the hair setting lotions according to the invention is generally between 3 and 8. As stated above, it is possible to regulate the pH to the desired value by using mono-or di-or triethanolamine and as acidifying agents, acetic acid or lactic acid.

The setting lotions according to the invention can contain only the dyes of Formula I, in which case they constitute what is known as shading compositions. However, the hair-setting lotions of this invention can also contain other direct dyes such as anthraquinone dyes, nitro dyes of the benzene series and those mentioned above. The hair-setting lotions can also contain various ingredients usually used in capillary cosmetics, for example, wetting agents, dispersing agents, swelling agents, penetrating agents, thickeners, softeners or perfumes, as mentioned above. The hair-setting lotions disclosed herein are used in the customary manner by application at ambient temperature to wet hair that has been previously washed and rinsed, followed by rolling the hair up on curlers and drying of the hair.

In another embodiment of the present invention, the dyes of Formula I can also be used in the production of hair lacquers. These lacquers contain in alcohol solution, at least one cosmetic resin and at least a compound of Formula I.

The alcohols suitable for the preparation of the hair lacquers according to the invention are low molecular weight alkanols, such as ethanol or isopropanol. As resins there may be employed one or more of those including polyvinyl pyrrolidone, copolymers of crotonic acid and vinyl acetate, copolymers of vinyl pyrrolidone and vinyl acetate, copolymers of maleic anhydride and butylvinyl ether, all as described above. The amount of dye of Formula I ranges from about 0.001 to about 0.5% by weight and the amount of cosmetic resin used is between about 1 and 3% by weight. Of course the hair lacquers of the present invention are conveniently packaged in pressurized containers or aerosol bombs of the type described above. The hair lacquers are conveniently applied directly to the hair, preferably in the form of a spray at ambient temperature.

Of the dyes of Formula I as described above, there are a certain number of novel compounds which are also part of and comprise another embodiment of the present invention.

Thus, the present invention in the composition of matter aspect thereof, includes novel diazamerocyanines and salts thereof of the formula $$A=N-N=B'' \qquad (I')$$

wherein

A is a nitrogen heterocycle as defined above and B" is a residue corresponding to one of the following formulae:

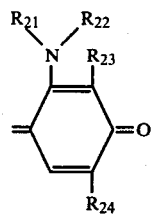

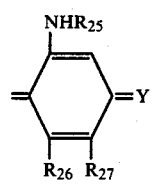

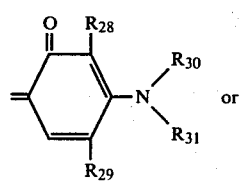

or

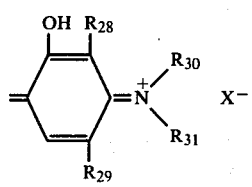

In the above formulae $X^-$ represents an anion derived from an inorganic or organic acid;

$R_{21}$ is selected from the group consisting of hydrogen or lower alkyl having 1-4 carbon atoms;

$R_{22}$ is hydrogen, lower alkyl having 1-4 carbon atoms, lower alkyl having 1-4 carbon atoms substituted by an amine, lower alkyl having 1-4 carbon atoms substituted by an amide, and

wherein W is selected from the group consisting of hydrogen and sulfur, and R' is selected from the group consisting of amino and lower alkyl of 1-4 carbon atoms, $R_{23}$ and $R_{24}$ each independently represent a member selected from the group consisting of hydrogen and lower alkyl having 1-4 carbon atoms;

Y represents a member selected from the group consisting of

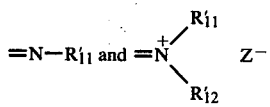

wherein $R_{11}'$ and $R_{12}'$ each independently represent a member selected from the group consisting of hydrogen and lower alkyl having 1-4 carbon atoms, and $Z^-$ is an anion derived from an inorganic or organic acid, such as halide, perchlorate, fluoborate, acetate, bisulfate and sulfate;

$R_{25}$ represents a member selected from the group consisting of hydrogen and

wherein W represents a member selected from the group consisting of oxygen and sulfur, and R' represents a member selected from the group consisting of amino and lower alkyl having 1-4 carbon atoms, $R_{26}$ and $R_{27}$ each independently represent a member selected from the group consisting of hydrogen, lower alkyl having 1-4 carbon atoms and methoxy, provided that $R_{27}$ represents hydogen when $R'_{11}$, $R'_{12}$ and $R_{25}$ represent hydrogen: $R_{28}$ and $R_{30}$, together with the carbon and nitrogen atoms to which they are attached, represent a member selected from the group consisting of a saturated heterocycle containing 5 ring atoms, an unsaturated heterocycle containing 5 ring atoms, a saturated heterocycle containing 6 ring atoms, an unsaturated heterocycle containing 6 ring atoms, in which case $R_{29}$ represents hydrogen and $R_{31}$ represents a member selected from the group consisting of hydrogen and lower alkyl having 1-4 carbon atoms;

Or $R_{29}$ and $R_{31}$, together with the nitrogen atoms to which they are attached, represent a member selected from the group consisting of a saturated heterocycle containing 5 ring atoms, an unsaturated heterocycle containing 5 ring atoms, a saturated heterocycle containing 6 ring atoms, an unsaturated heterocycle containing 6 ring atoms, in which case $R_{28}$ represents hydrogen and $R_{30}$ represents a member selected from the group consisting of hydrogen, lower alkyl having 1-4 carbon atoms and acyl having 2 to 5 carbon atoms.

These novel compounds according to the present invention are obtained by known processes, including condensation of a hydrazene of the general formula

wherein A has the definitions set forth above, with a complex corresponding to one of the following formulae:

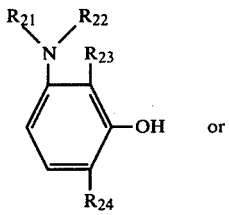

or

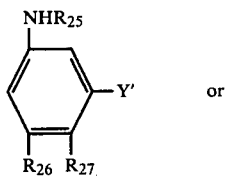

or

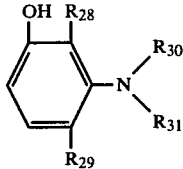

where Y' designates a residue

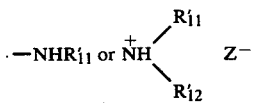

and radicals $R_{21}$ to $R_{31}$ and $R'_{11}$, $R'_{12}$ and Z have the signification indicated above, this condensation being performed in the presence of an oxidizing agent which can be hydrogen peroxide, an alkaline persulfate, an alkaline chlorite, potassium ferricyanide or ferric chloride, at a temperature between 15° and 70° C., either in an alkaline medium or an acid medium, in case it is desired to obtain a compound with a quaternary ammonium group. The acid used can be that corresponding to the desired salt, or a different acid, in which case the condensation is followed by an addition to the reaction medium of a salt of the acid corresponding to the desired diazamerocyanine salt that is more soluble in water than said diazamerocyanine salt, which is then isolated by filtering. This method of preparation has been generally described in S. Hunig in "Angewandte Chemie", International Edition, Volume 7, pages 335–344 (1968), the disclosure of which is hereby incorporated by reference.

The subject matter of this application includes new dyeing compositions as well as some new azo dyes. These compositions are useful in dyeing keratinous fibers, particularly human hair, and may be used as hair setting lotions, hair dye and hair lacquer.

Thus the invention is directed to these new compositions, new dyes and to process for dyeing using said composition.

The applicants have discovered compositions containing dyes of the formula

  (IA)

in which A' is a nitrogen heterocycle of six carbon atoms of the formula

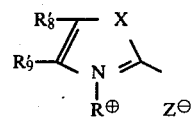

where R is an alkyl group containing 1 to 4 carbon atoms, X is an ethylenic group, and B' is a radical of the formula

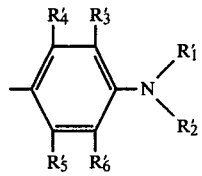

wherein the ethylenic group corresponds to the formula

wherein the dyes of the invention correspond to the general formula

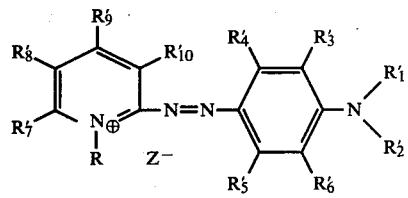  (IIA)

in which:

$R'_{10}$ represents a hydrogen atom or a lower alkyl group of 1 to 4 carbon atoms, preferably methyl;

$R'_9$ represents a hydrogen atom, an alkyl group of 1 to 4 carbon atoms, preferably methyl, or a —CN group;

$R'_8$ represents a hydrogen atom; a halogen atom, preferably chlorine, or alkyl of 1 to 4 carbon atoms, preferably a methyl group;

$R'_7$ represents a hydrogen atom, an alkyl group containing an alkyl of 1 to 4 carbon atoms, preferably a methyl group; or a —CN group;

$R'_1$ is a hydrogen atom; an alkyl group containing an alkyl of 1 to 4 carbon atoms; or a hydroxyalkyl group, containing an alkyl of 1 to 4 carbon atoms; preferably β-hydroxyethyl;

$R'_2$ is a hydrogen atom, an alkyl group of 1 to 4 carbon atoms, a hydroxyalkyl of 1 to 4 carbon atoms, preferably β-hydroxyethyl or phenyl;

$R'_3$ is a hydrogen atom, an alkyl group of 1 to 4 carbon atoms, preferably methyl, or an alkoxy group of 1 to 4 carbon atoms, preferably methoxy;

$R'_4$ is a hydrogen atom;

$R'_5$ is a hydrogen atom, a hologen atom, preferably chloro, an alkyl group of 1 to 4 carbon atoms, and preferably methyl; nitro; amino or acetylamino;

$R'_6$ is a hydrogen atom; and wherein $R'_5$ and $R'_6$, joined together, can form an unsaturated cyclic ring of 6 carbon atoms substituted by an hydroxy substituent which chelates with the nitrogen atoms of the azo bond, and then, $R'_1$, $R'_2$, $R'_3$, $R'_4$ are hydrogen, $Z^-$ can be an anion derived from a mineral (inorganic) or an organic acid and may be halogen, as iodine, chlorine, bromine, fluoroborate, perchlorate, sulfate, bisulfate, acetate and in particular methylsulfate or its mesomeric form.

The quaternary nitrogen dyes may be defined by the formula showing the mesomeric forms of the dyes:

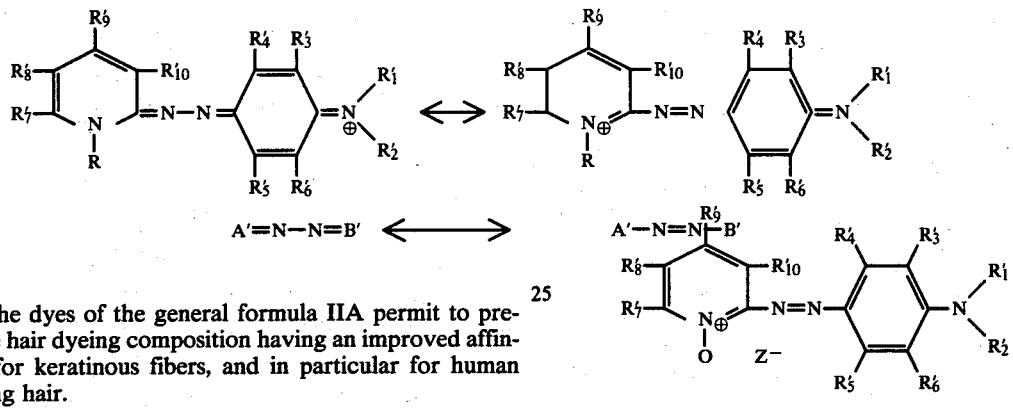

The dyes of the general formula IIA permit to prepare hair dyeing composition having an improved affinity for keratinous fibers, and in particular for human living hair.

In addition, the compositions of the invention are characterized by an improved stability to light.

Compared to known dyes, and compared to those described in the parent application, the dyes presented herein offer the advantage of an increased solubility in solvents typically used in cosmetics, such as water, alcohols and their mixtures.

The compounds of the general formula IIA which are useful in accordance with the invention, are prepared from reactants of the general formula

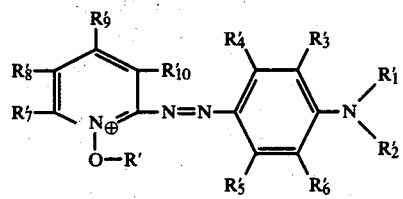

as described in French application serial No. 73 22 158.

Among the compounds, are included salts of 1'-(4'-dialkyl-aminobenzene)2-azo pyridinium, in which the pyridinium ring is not substituted in the 3 and 4 position but which may eventually be substituted in the 5 and 6 position by a methyl group, and in particular the salts of methyl sulfate of these compounds.

Other compounds which are particularly interesting and known are those including the salts of 1'-(4'-dialkylaminobenzene) 2-azo 1-alkyl pyridinium in which the pyridinium ring is substituted in the 3 or the 4 position and those which may be eventually substituted in the 5 and/or 6 position by a methyl group or by a chloroatom in the 5 position. In addition, known compounds which are useful in the composition in accordance with the invention include compounds substituted in the 5 position by a chlorine atom and in which the 3 and 4 positions on the pyridine nucleus are not substituted.

The benzene ring of these compounds may be substituted in the 2' position by a chlorine atom, a methyl, nitro, amino or acetyl amino group; in the 5 position by a methyl or methoxy group.

The amino group in the 4' position may be substituted by alkyl groups such as methyl or ethyl or by a hydroxyalkyl group, such as β-hydroxyethyl.

The new compounds of the general formula (IIA) useful in the compositions in accordance with the invention correspond to the general formula

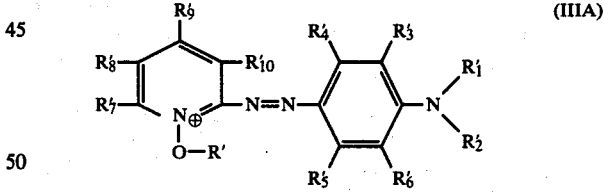

in which $R'_{10}$, $R'_8$, $R'_3$, $R'_4$, $R'_5$, $R'_6$, $R'_1$, $R'_2$ have the same definition as those set forth in the general formula IIA and wherein $R'_9$ or $R'_7$ can be a cyano group.

Other new compounds which may be used in the compositions of the invention include compounds corresponding to the general formula IIA in which $R'_9$ and $R'_7$ are different from a cyano group, wherein $R'_5$ and $R'_6$ form an unsaturated ring of 6 carbon atoms containing the hydroxy substituent chelated with the nitrogen atom in the azo bond, in which case, $R'_1$, $R'_2$, $R'_3$ and $R'_4$ are hydrogen. The compounds corresponding to the general formula IIA are prepared by a process comprising providing reactants of the general formula IIIA (IIIA)

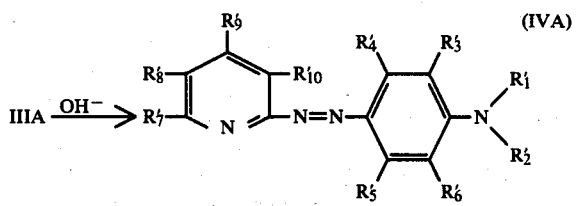

which was described in French Pat. No. 7322158. These compositions are treated with alkali in a manner to obtain a compound of the general formula IVA according to the equation set forth below.

(IVA)

IIIA $\xrightarrow{OH^-}$

The compounds of the general formula IVA are then treated with an alkylating agent RZ, wherein R and Z correspond to the definitions set forth above with respect to the compounds of the general formula IIA, according to the following reaction.

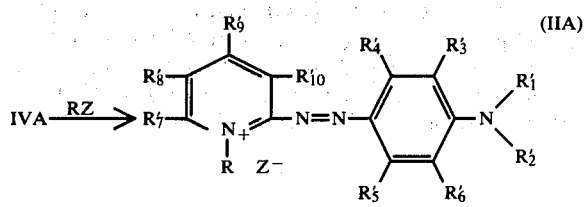

In one embodiment of the invention, the invention seeks to provide dyes for keratinous fibers, in particular for human hair, which are dye compositions in the solution form.

The compositions according to the invention are aqueous solutions or alcoholic solutions which may be easily prepared by dissolving 1 or more compounds of the general formula IIA in water or in mixtures of water and alcohol.

The concentrations of compounds of the general formula IIA in the dye compositions according to the invention may be varied over wide ranges, by reason of the great affinity of these compounds for keratinous fibers. The concentration of these dyes (IIA) is generally between 0.0001 and 5% by weight, and preferably between 0.01 and 1.5% by weight of the dye composition.

The pH of the dye compositions in solution is generally between 3 and 12. The pH may be adjusted to any desired value by addition of an acid such as orthophosphoric acid, citric acid, acetic acid or by the addition of a base such as triethanolamine, monoethanolamine, or ammonia.

The compositions according to the invention may contain only dyes of the general formula IIA, which compositions may be applied to hair to impart rich nuances in hair color which range from orange to blue in light.

The compositions may be mixed with other direct dyes, for example azo dyes or anthraquinone dyes, nitro benzene dyes, indoanilines, indophenols or indamines.

The compositions of the invention may include in addition to compounds of the formula IIA other additives used generally in cosmetics, for example softening agents, dispersing agents, swelling agents, agents to increase penetration, emollients and perfumes. In addition, the dye compositions of the invention may contain reagents necessary for packaging compositions of the invention in aerosol cans. In addition, the composition of the invention can contain surface active agents such as sulfates of lower alcohols, ethanolamides of lower alcohols, and acids, esters, and alcohols of polyoxethylenes.

Dyeing the human hair with the aid of the compositions in accordance with the invention may be effected by conventional steps for applying dye compositions to the hair, which steps include contacting the hair for a period of 3 to 30 minutes with the dye compositions, and following this application, with a rinse, with a wash, and then drying the hair.

The present invention also is directed to dye lotions which are capillary hair setting lotions which are mixtures, or solutions, of aqueous alcohol solutions with a cosmetic resin and at least one dye of the formula IIA, as described above. The lotions according to the invention generally contain 20 to 70% by weight of an alcohol based on the molecular weight of the dye and 1 to 3% by weight of the cosmetic resin.

Among resins which are used in cosmetics and which are useful in compositions in accordance with the invention, are film-forming polymers such as polyvinylpyrrolidone, copolymers of polyvinylpyrrolidone-vinyl acetate, copolymers of vinyl acetate and unsaturated carboxylic acid, such as crotonic acid, copolymers resulting from copolymerization of vinyl acetate, crotonic acid and an acrylic ester or a methacrylic ester, the copolymers resulting from the copolymerization of vinyl acetate and alkyl vinyl ether, copolymers resulting from the copolymerization of vinyl acetate, crotonic acid and a vinylic ester of an acid of a long chain hydrocarbon, or an allylic ester or methallylic ester of an acid of a long chain hydrocarbon; copolymers resulting from the copolymerization of an ester derived from an unsaturated alcohol and an acid of a lower alkyl, an unsaturated acid of a lower alkyl and at least one ester derived from a saturated alcohol of a lower alkyl, and an unsaturated acid, the copolymers resulting from the copolymerization of an unsaturated ester and at least one unsaturated acid.

The preferred resins include for instance, polyvinyl pyrrolidone having a molecular weight between 10,000 and 70,000; copolymers of 10% crotonic acid and 90% vinyl acetate characterized by weight of between 10,000 and 70,000; copolymers of polyvinyl pyrrolidone and vinyl acetate having a molecular weight ranging between 30,000 and 200,000, the ratio of polyvinyl pyrrolidone: vinyl acetate being between 30:70 and 70:30; copolymers of maleic anhydride and methyl vinyl ether in which the molar ratio respectively, is preferably 1:1, and wherein the viscosity is between 0.1 and 3.5, measured at 25° C., at a concentration of 1 gram of copolymer in 100 $cm^3$ methylethyl ketone; monethyl esters, monoisopropyl esters and monobutyl esters of copolymers of maleic anhydride and methyl vinyl ether; the copolymers of maleic anhydride and of butyl vinyl ether, wherein the molar ratio of maleic anhydride to butyl vinyl ether ranges between 1:1; terpolymers containing 15 to 25% methylmethacrylate, 18 to 28% stearyl methacrylate and 52 to 62% dimethyl aminoethyl methacrylate, quaternized by dimethyl sulfate; pure polymers containing 75 to 85% vinyl acetate, 10 to 20% allyl stearate, and 3 to 10% of allyloxy acetic acid. These resins are incorporated in that composition in proportions between 1 to 3% by weight.

Low molecular weight alcohols are used as solvents to obtain the lotions in accordance with the invention, and include preferably ethanol and isopropanol.

The pH of the lotions which are solutions and compositions in accordance with the invention generally ranges between 3 and 9.

Compositions, which are lotions of solutions in accordance with the invention, may include the dyes of formula (IIA), in which case such compositions are conventionally referred to as hair tints. Also, the compositions can include other direct dyes such as those mentioned above. The compositions of the invention may in addition include additives such as those recited above.

Setting lotions in accordance with the invention may be used in the conventional manner, by applying to damp hair, previously washed and rinsed, followed by rolling and drying the hair.

The dyes of formula (IIA) may equally be used in the form of hair lacquers, by including in an alcoholic solution containing the dyes of formula (IIA) at least one cosmetic resin, as well as the dye (IIA).

The alcohols utilized in lacquers according to the invention are low molecular weight alcohols, such as ethanol or isopropanol.

Cosmetic resins used in accordance with such hair lacquers, may be those disclosed above. Such resins are included in the composition in amounts of 1 to 3% by weight of the composition.

Thus the present invention has as an object dyeing compositions for human hair characterized in that they contain in an aqueous solution having a pH between about 3 and about 9, from 0.0001 to 0.5% by weight of a least one diazamerocyanine including the mesophormic forms thereof, having the formula

A=N—N=B wherein A represents a nitrogen heterocycle selected from the group consisting of

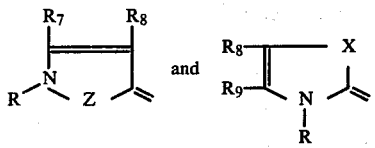

wherein R represents a member selected from the group consisting of lower alkyl having 1-4 carbon atoms and phenyl;

X represents a member selected from the group consisting of oxygen; sulfur; —NR'—, wherein R' represents lower alkyl having 1-4 carbon atoms; —CR'$_9$=CR'$_{10}$— wherein R'$_9$ is a hydrogen atom, an alkyl group of 1 to 4 carbon atoms or a cyano and wherein R'$_{10}$ is a hydrogen or an alkyl of 1 to 4 carbon atoms;

—C=N,
 |
 R"

wherein R" represents a member selected from the group consisting of hydrogen and lower alkyl having 1-4 carbon atoms, and —C(R") (R")—, wherein R" each independently having the meaning given above, Z represents a member selected from the group consisting of —CH=CH— and —NR''', wherein R''' represents lower alkyl having 1-4 carbon atoms;

R$_7$ represents a member selected from the group consisting of hydrogen, lower alkyl having 1-4 carbon atoms, cyano and phenyl;

R$_8$ represents a member selected from the group consisting of hydrogen, halogen and lower alkyl having 1-4 carbon atoms, provided that R$_7$ and R$_8$, when taken together with the carbon atoms to which they are linked, represent a member selected from the group consisting of a benzene ring, a halogen-substituted benzene ring, a benzene ring substituted with lower alkyl having 1-4 carbon atoms, a benzene ring substituted with lower alkoxy having 1-4 carbon atoms and a nitrosubstituted benzene ring;

B represents a member selected from the group consisting of (i) a nitrogen-containing heterocycle different from the nitrogen-containing heterocycle of A;

(ii) a cycle of the formula

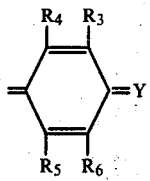

wherein Y represents a member selected from the group consisting of oxygen and

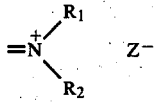

wherein R$_1$ and R$_2$ each independently represent a member selected from the group consisting of hydrogen, lower alkyl having 1-4 carbon atoms, hydroxyalkyl having 1-4 carbon atoms, and phenyl; and Z$^-$ is an anion derived from a member selected from the group consisting of an inorganic acid and an organic acid;

R$_3$ represents a member selected from the group consisting of hydrogen, lower alkyl, lower alkoxy and phenylcarbamyl, R$_4$ and R$_6$ each independently represent a member selected from the group consisting of hydrogen, lower alkyl having 1-4 carbon atoms and lower alkoxy having 1-4 carbon atoms, and R$_5$ represents a member selected from the group consisting of hydrogen, halogen, alkyl of 1 to 4 carbon atoms, nitro, amino, allkylated amino having 1-4 carbon atoms, acylated amino having 2-5 carbon atoms; R$_5$ and R$_6$ being able, together with the carbon atoms to which they are attached to form unsaturated 6 member ring;

(iii) a group having the formula

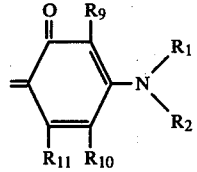

wherein R$_1$ and R$_9$, together with the nitrogen and carbon atoms to which they are attached, represent a compound selected from the group consisting of a saturated heterocycle having 5 ring atoms, an unsaturated heterocycle having 5 rings atoms, a saturated heterocycle having 6 rings atoms, an unsaturated heterocycle having 6 rings atoms, in which case R$_{10}$ is hydrogen and R$_2$ represents a member selected from the group consisting of hydrogen and lower alkyl having 1-4 carbon atoms; and wherein R$_2$ and R$_{10}$, when taken together with the nitrogen and carbon atoms to which they are attached, represent a compound selected from the group consisting of a saturated heterocycle having 5 rings atoms, an unsaturated heterocycle having 5 ring atoms, a saturated heterocycle having 6 ring atoms and an unsaturated heterocycle having 6 ring atoms, in which case R$_9$ is hydrogen and R$_1$ represents a member selected from the group consisting of hydrogen, lower alkyl having 1-4 carbon atoms and acyl having 2 to 5 carbon atoms, and R$_{11}$ represents a member selected from the group consisting of hydrogen and lower alkyl having 1-4 carbon atoms; and (iv) a group having the formula

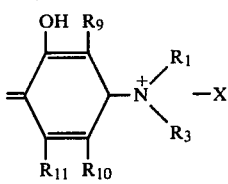

wherein $R_1$, $R_2$, $R_9$, $R_{10}$ and $R_{11}$ have the meaning given above and $X^-$ represents an anion derived from a member selected from the group consisting of an inorganic acid and an organic acid.

The present invention has also as object new compounds useful in the compositions as defined above which are dialomerocyanine or their mesophormic form, having the general formula

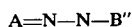

wherein A and B" have the meanings above-mentioned and wherein X means also $-CR'_9=CR'_{10}-$ wherein $R'_9$ is a hydrogen atom, an alkyl group of 1 to 4 carbon atoms or a cyano and wherein $R'_{10}$ is a hydrogen or an alkyl of 1 to 4 carbon atoms $R_7$ means also cyano $R_8$ means also halogen and B" may be also

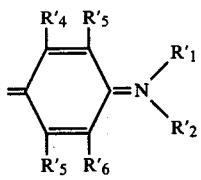

wherein $R'_1$, $R'_2$, $R'_3$, $R'_4$, $R'_5$, $R'_6$ have the meanings above-mentioned, with the proviso that at least one of $R_7$ or $R'_9$ means cyano or $R'_5$ and $R'_6$ bonded together form an unsaturated 6 member ring, containing an hydroxy substituent which chelates with the nitrogen atom of the azo group and each of $R'_1$, $R'_2$, $R'_3$ and $R'_4$ is then hydrogen, $R_7$, $R_8$, $R'_9$, $R'_{10}$ having the different meanings above-mentioned The compositions may be used in the different forms, concentrations and admixtures as mentioned above.

The examples are illustrative of the invention and are not to be taken as limiting but as representative of all modifications, and equivalents known in the art.

The following examples are intended to illustrate various aspects of the present invention. Unless otherwise indicated, all parts and percentages are by weight and all temperatures used herein are expressed in degree centigrade.

EXAMPLE 1

3-methyl 2,3-dihydro 2:4'-azino benzothiazole 3'-amino 6'-methyl 1'-oxo 1',4'-dihydro benzene having the formula as indicated below is prepared as follows:

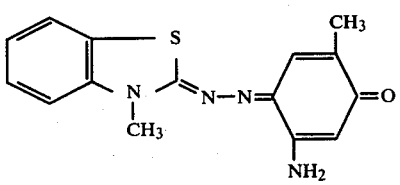

To a solution of 1.80 g of 3-methyl benzothiazolone hydrazone (0.01 mole) in 100 cc of 50% alcohol, a solution of 1.60 g of 3-amino 6-methyl phenol (0.01 mole) in 50 cc of 50% alcohol and 5 cc of ammonia at 22° Be are added successively. The mixture is maintained at 30° C. with stirring, then there is introduced a solution of 2.28 g of ammonium persulfate in 20 cc of 50% alcohol. Stirring is continued for 30 minutes, then the precipitate obtained is drained, washed with water and dried on phosphoric anhydride.

The dye is in the form of a reddish brown solid with a melting point above 260°.

Molecular weight found by potentiometric determination in glacial acetic acid with $HClO_4$ $N/10=297$, (the theoretical value is 298).

EXAMPLE 2

3-methyl 2,3-dihydro 2:4'-azino benzothiazole 2',6'-dimethyl 1'-oxo 1',4'-dihydro benzene having the formula below is prepared as follows:

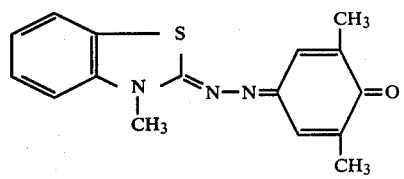

In a manner similar to that of Example 1, but using 2,6-dimethyl phenol for the 2-amino-6-methyl phenol, the above-indicated dye is obtained in form of a bright red solid with a melting point of 236°. Molecular weight was calculated in a similar manner as Example 1 and found by potentiometric determination to be 300 (theory: 297).

EXAMPLE 3

Preparation of 3-methyl 2,3-dihydro 2:4'-azino benzothiazole 3'-acetamino 6'-methyl 1'-oxo 1',4'-dihydro benzene having the formula below is prepared as follows:

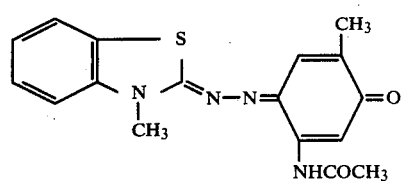

In a manner identical to that of Example 1, but using 3-acetamino-6-methyl phenol a reddish orange product is obtained with a melting point above 260°. Similarly, molecular weight was calculated by potentiometric determination and found to be 350 (theory: 340).

EXAMPLE 4

Preparation of 3-methyl 2,3-dihydro 2:4'-azino benzothiazole 3'-amino 2',6'-dimethyl 1'-oxo 1',4'-dihydro benzene having the formula below is prepared as follows:

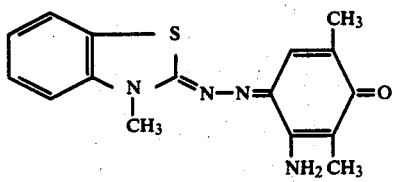

In a manner identical to that of Example 1, but using 3-amino-2,6-dimethyl phenol a brown product is obtained with a melting point of 250°.

Molecular weight was determined by potentiometric determination and found to be 321 (theory: 312).

EXAMPLE 5

3-phenyl 4-methyl 2,3-dihydro 2:4'-azino thiazole 1',4'-dihydro 1'-oxo 2'-naphthanilide having the formula below

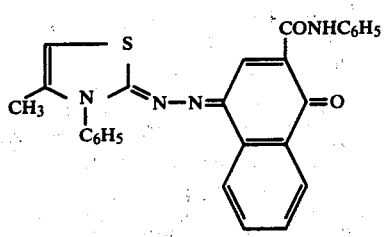

was prepared as described by S. Huenig in "Liebigs Annalen der Chemie", Vol. 47, p. 77, the disclosure of which is hereby incorporated by reference.

A red product is obtained with a melting point of 238°.

EXAMPLE 6

3,4-diphenyl 2,3-dihydro 2:4'-azino thiazole 1',4'-dihydro 1'-oxo 2'-naphthanilide having the following formula:

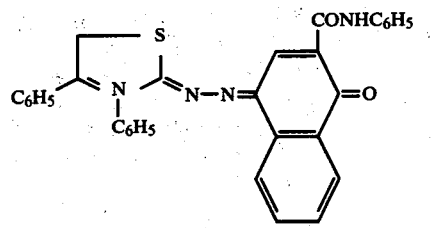

is prepared as described in Example 5, but using 3,4-diphenyl 2,3-dihydrothiazole.

A red product is obtained with a melting point of 240°.

EXAMPLE 7

2[(1-dimethylamino-phenyl (4)) azo]-3 methyl benzothiazolium perchlorate having the following formula:

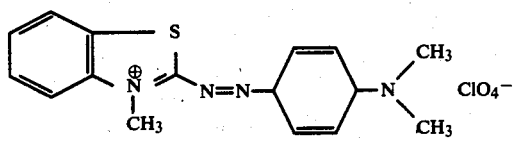

is prepared by the method described by S. Huenig in "Liebigs Annalen der Chemie", Vol. 628, p. 88, the disclosure of which is hereby incorporated by reference.

A product with green glints is obtained with a melting point of 230°.

EXAMPLE 8

1,3-dimethyl-2[(1-dimethylamino phenyl (4)) azo]imidazolium perchlorate having the following formula:

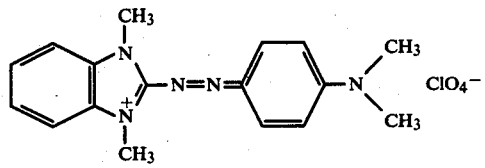

is prepared by the method described by S. Huenig in "Liebigs Annalen der Chemie", Vol. 628, p. 90, the disclosure of which is hereby incorporated by reference.

A product with green glints is obtained with a melting point of 242°.

EXAMPLE 9

2[(1,3-diamino 6-methyl-phenyl (4)) azo]-3 methyl benzothiazolium iodide having the below formula, is prepared as follows:

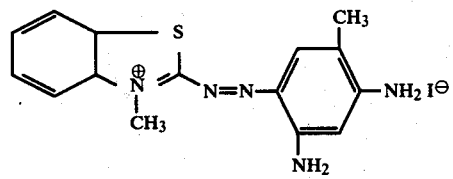

1.80 g of N-methyl benzothiazolone hydrazone are dissolved in 160 cc of normal hydrochloric acid containing 10 mg of ferrous sulfate. 1.22 g of meta-toluylene diamine are added and thereafter 2.5 cc of 30% hydrogen peroxide are added with stirring. The reaction mixture is stirred for a half hour at 30° C., then 10 cc of formic acid are added. The reaction mixture is next heated to 70° C., it is filtered and 2.2 g of potassium iodide are added to the filtrate. After cooling the precipitate is drained, washed with water and dried on phosphoric anhydride.

The dye is obtained in the form of a reddish violet solid with a melting point of 180° (decomposition).

EXAMPLE 10

2[1,3-diamino 2,6-dimethyl phenyl (4)) azo]-3 methyl benzothiazolium iodide having the below formula

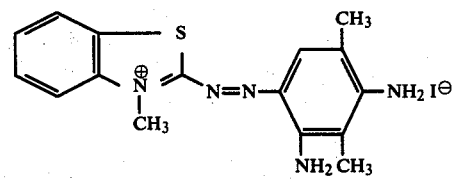

is prepared in a manner identical with that of Example 9, except that 1,3-diamino 2,6-dimethyl phenol is employed.

The dye is isolated in the form of a reddish violet solid with a melting point of 170° (decomposition).

EXAMPLE 11

3-methyl 2,3-dihydro 2:4'-azino benzothiazole 1'-phenyl 3'-methyl 4'-ylidene 5'-pyrazolone of the below formula is prepared as follows:

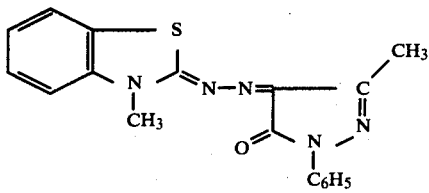

1.80 g of N-methyl benzothiazolone hydrazone are dissolved in 200 cc of 50% methanol. A solution of 1.74 g of 1-phenyl-3-methyl-5-pyrazolone in 50 cc of 50% methanol are added and then a solution of 14.5 g of potassium ferricyanide in a mixture of 100 cc of 50% methanol and 10 cc of 25% ammonia are introduced with stirring. The reaction mixture is stirred for a half hour, then 300 cc of water are added. The precipitate that results is drained, washed with water and dried on phosphoric anhydride. The dye obtained is in the form of a reddish orange solid with a melting point of 262°.

EXAMPLE 12

1,3-dimethyl 2,3-dihydro 2:4'-azino benzimidazole 1'-phenyl 3''-methyl 4'-ylidene 5'-pyrazolone of the below formula:

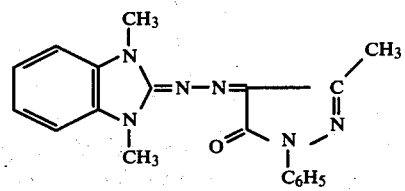

is prepared in a manner identical with that of Example 11, except that 1,3-dimethyl 2,3-dihydro benzimidazolone hydrazone is employed.

The dye is isolated in the form of a reddish orange product with a melting point of 268°.

EXAMPLE 13

1,2-dimethyl 2,3-dihydro 2:4'-azino indazole 1'-phenyl 3'-methyl 4'-ylidene 5'-pyrazolone of the below formula

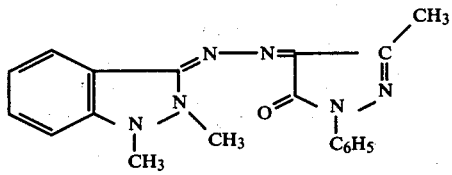

is prepared in a manner similar to that of Example 11.

The dye is obtained in the form of a brownish orange product with a melting point of 264°.

Molecular weight calculated by potentiometric determination was found to be 348 (theory: 346).

EXAMPLE 14

4-methyl 3-phenyl 2,3-dihydro 2:4'-azino thiazole 1'-phenyl 3'-methyl 4'-ylidene 5'-pyrazolone of the below formula

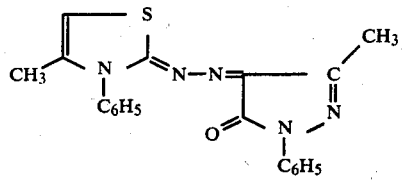

is prepared in a manner similar to that described in Example 11.

An orange product is obtained with a melting point of 232°.

EXAMPLE 15

1-methyl 1,4-dihydro 4:4'-azino pyridine 1',4'-dihydro 1'-oxo benzene of the below formula:

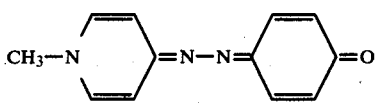

is prepared in a manner as described by S. Huenig in "Liebigs Annalen der Chemie", Vol. 636, p. 27, the disclosure of which is hereby incorporated by reference.

A dye is obtained in the form of a deep violet solid with a melting point of 213°.

EXAMPLE 16

1-methyl 1,4-dihydro 4,4'-azino pyridine 1',4'-dihydro 1'-oxo naphthalene of the below formula:

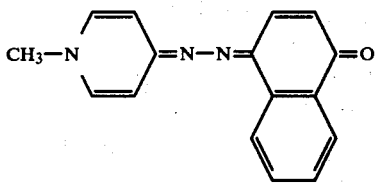

is prepared by the process as described by S. Huenig in "Liebigs Annalen der Chemie", Vol. 636, p. 28, the disclosure of which is hereby incorporated by reference.

The dye is obtained in the form of a solid with green glints with a melting point of 225°.

EXAMPLE 17

1,2-dimethyl 2,3-dihydro 3:7'-azino indazole 6'-oxo 6',7'-dihydro benzomorpholine of the below formula, is prepared as follows:

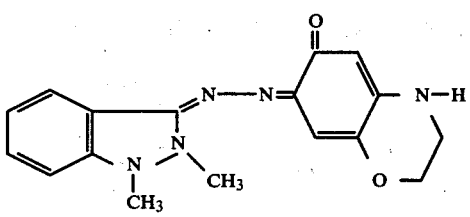

2.12 g of 1,2-dimethyl 3-indazolone hydrazone hydrochloride are dissolved in 80 cc of water. At ambient temperature a solution of 1.51 g of 6-hydroxy benzomorpholine in 80 cc of water is added, then, with stirring, in 15 minutes a solution of 4.56 g of ammonium persulfate and 12 cc of ammonia at 22° Be is added. Stirring is continued for 30 minutes, followed by filtering, washing with cold water and drying of the precipitate thus obtained on phosphoric anhydride. The product obtained is a brownish red dye with a melting point of 230°.

EXAMPLE 18

1,3-dimethyl 1,2-dihydro 2:7'-azino benzimidazole 6'-oxo 6',7'-dihydro benzomorpholine of the below formula:

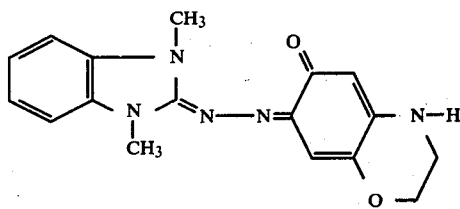

is prepared in a manner identical with that described in Example 17. The dye is obtained in the form of a brown solid with green glints having a melting point of 184°.

Molecular weight found: 324.
Molecular weight calculated (theoretical): 323.

EXAMPLE 19

3-methyl 2,3-dihydro 2:7'-aminobenzothiazole 6'-oxo 6',7'-dihydro benzomorpholine of the below formula:

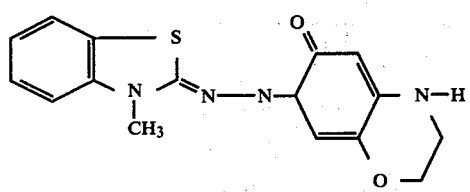

is prepared in a manner identical with that described in Example 17. The dye is obtained in the form of a brown solid with a melting point of 195°.

EXAMPLE 20

7'-(6'-hydroxy benzomorpholine) 2-aza 3-methyl benzothiazolium chloride of the below formula, is prepared as follows:

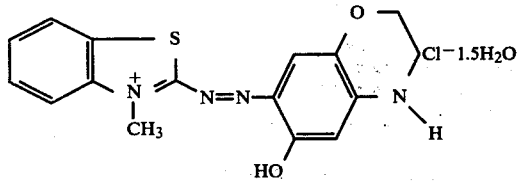

2.52 g (0.01 mole) of N-methylbenzothiazolone hydrazone dihydrochloride and 1.51 g (0.01 mole) of 6-hydroxy benzomorpholine are dissolved in 200 cc of 1 N HCl, then, over a period of 45 minutes, 26 cc of 28% $FeCl_3$ dissolved in 24 cc of water is added. The mixture takes on a violet shade and a precipitate appears. The reaction mixture is allowed to react for 15 minutes, then filtered and the product dried under vacuum on phosphoric anhydride. The chloride thus obtained is purified by dissolving in dimethylformamide and reprecipitation with water. Melting point: 225° C. (decomposition).

Analysis: C%: 48.66–48.66 (49.3 theoretical); H%: 3.87–3.99 (4.62 theoretical); N%: 14.35–15.51 (14.12 theoretical).

EXAMPLE 21

7'-(6-hydroxy benzomorpholine) 2-aza 3-methyl benzothiazolium perchlorate is obtained by dissolving of the chloride prepared in Example 1 in a suitable quantity of acetic acid and reprecipitation by sodium perchlorate.

Analysis: C%: 42.69–42.46 (42.40 theoretical); H%: 3.62–3.68 (3.97 theoretical); N%: 12.43–12.55 (12.37 theoretical).

The melting point was found to be 240° C. (decomposition).

EXAMPLE 22

7'-(6'-hydroxy benzomorpholine) 2-aza 4-methyl 3-phenyl thiazolium perchlorate of the below formula, is prepared as follows:

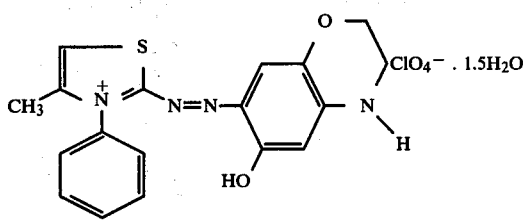

3.45 g (0.01 mole) of 4-methyl 3-phenyl thiazolone benzene sulfonylhydrazone and 1.51 g (0.01 mole) of 6-hydroxy benzomorpholine are dissolved in 100 cc of crystallizable acetic acid. Thereafter, in 15 minutes about 2.28 g (0.01 mole) of ammonium persulfate in 10 cc of water is added and the solution taken on a violet tint. The reaction mixture is stirred for 30 minutes, then 5 g of sodium perchlorate dissolved in 20 cc of water are added. The reaction mixture is again stirred for 1 hour, then filtered and dried under vacuum on phosphoric anhydride.

The product is purified by dissolving in a suitable quantity of dichlorethane, filtering of the insoluble material and reprecipitation by carbon tetrahydrochloride. A powder with green glints is obtained with a melting point of 230°.

Analysis: C%: 45.18–44.70 (54.04 theoretical); H%: 4.07–3.94 (4.17 theoretical); N%: 11.69–11.84 (11.68 theoretical).

EXAMPLE 23

7'-(6'-hydroxy benzomorpholine) 2-azo 3,4-diphenyl thiazolium perchlorate of the below formula, is prepared as follows:

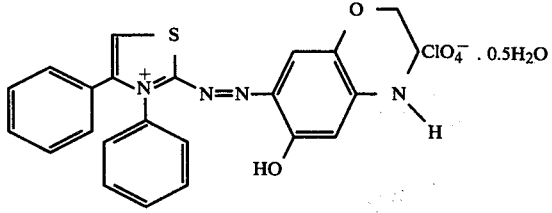

1.33 g (0.005 mole) of 3,4-diphenyl thiazolone hydrazone and 0.75 g (0.005 mole) of 6-hydroxy benzomorpholine are dissolved in 50 cc of crystallizable acetic acid. 2.28 g (0.01 mole) of ammonium persulfate dissolved in 10 cc of water are added in 30 minutes and an intense violet coloring appears. After stirring the reaction mixture for 30 minutes, 2 g of sodium perchlorate dissolved in 10 cc of water are added. The reaction mixture is filtered, washed with water and dried under a vacuum on phosphoric anhydride.

The product is purified by dissolving in a sufficient quantity of dichlorethane and precipitation by carbon tetrachloride, there being obtained crystals with green glints with a melting point of 170° C.

Analysis: C%: 52.57–52.60 (52.75 theoretical); H%: 4.38–4.10 (3.82 theoretical); N%: 10.05–10.29 (10.7 theoretical).

Determination by water (Karl Fisher): 1.5%.

EXAMPLE 24

7'-(6'-hydroxy benzomorpholine) 2-azo 1,3 dimethyl benzimidazolium perchlorate of the below formula, is prepared as follows:

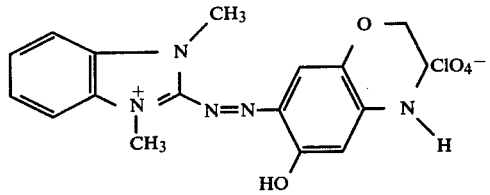

10 g (0.04 mole) of N,N'-dimethyl benzimidazolone hydrazone dihydrochloride and 6.04 g (0.04 mole) of 6-hydroxy benzomorpholine are dissolved in 250 cc of acetic acid. 30 g of sodium acetate dissolved in 100 cc of acetic acid are added and then, in about 30 minutes, 18.24 g (0.08 mole) of ammonium persulfate dissolved in 100 cc of water are added. The mixture is allowed to react for 30 minutes, then the inorganic salts are separated by filtering and the product is precipitated by addition of 20 g of sodium perchlorate dissolved in 300 cc of water. 9 g of the product are collected, corresponding to a yield of 70%, which is purified by extraction with methanol and concentration. The melting point was found to be 240° C.

Analysis: $C_{17}H_{18}N_5O_2 \cdot ClO_4$; C%: 48.6 (48.2 theoretical); H%: 4.6 (4.2 theoretical).

The following examples relate to another embodiment of the present invention wherein the dyes produced in the preceding examples are used in hair-setting lotions as hereinbefore described.

EXAMPLE 25

The following hair-setting lotion is prepared

| | |
|---|---|
| Dye of Example 8 | 0.100 g |
| Vinyl pyrrolidone-vinyl acetate copolymer (Vinyl pyrrolidone — 70%, vinyl acetate — 30%, molecular weight 35,000–45,000) | 3 g |
| Ethyl alcohol, 96° titer | 50 cc |
| Triethanolamine, q.s.p. | pH 5 |
| Water, q.s.p. | 100 cc |

This hair-setting lotion when applied to hair dyed brown, imparts thereto a purplish brown shade.

EXAMPLE 26

The following hair-setting lotion is prepared:

| | |
|---|---|
| Dye of Example 7 | 0.1 g |
| Vinyl acetate-crotonic acid copolymer (vinyl acetate — 90%, crotenic acid — 10%, molecular weight 45,000–50,000) | 2 g |
| Ethyl alcohol, 96° titer | 50 cc |
| Benzylidene camphor | 0.2 g |
| Triethanolamine, q.s.p. | pH 7 |
| Water, q.s.p. | 100 cc |

This hair-setting lotion when applied to hair dyed deep blond, imparts thereto a luminous ash glint.

EXAMPLE 27

The following dyeing composition is prepared:

| | |
|---|---|
| Dye of Example 7 | 0.0012 g |
| Vinyl pyrrolidone-vinyl acetate copolymer (vinyl pyrrolidone — 70%, vinyl acetate — 30%, molecular weight — 35,000–45,000) | 2 g |
| Ethyl alcohol, 96° titer | 50 cc |
| 200 volume hydrogen peroxide | 5 g |
| Orthophosphoric acid, q.s.p. | pH 3 |
| Water, q.s.p. | 100 cc |

This hair-setting lotion is applied at ambient temperature to naturally light brown hair. After setting and drying, the hair is lightly brightened and imparts thereto a pearly glint.

EXAMPLE 28

The following composition is prepared:

| | |
|---|---|
| Dye of Example 7 | 0.0015 g |
| Ethyl alcohol, 96° titer | 50 cc |
| 200 volume hydrogen peroxide | 5 g |
| Orthophosphoric acid, q.s.p. | pH 3 |
| Water, q.s.p. | 100 cc |

This composition is applied to naturally dark blond hair. After setting and drying the hair is lightly brightened up and the lotion imparts thereto an ash rose glint.

EXAMPLE 29

The following dyeing composition is prepared:

| | |
|---|---|
| Dye of Example 1 | 0.0006 g |
| Dye of Example 8 | 0.0006 g |
| Vinyl acetate-crotonic acid copolymer (vinyl acetate — 90%, crotonic acid — 10%, molecular weight 45,000–50,000) | 2 g |
| Ethyl alcohol, 96° titer | 55 cc |
| 200 volume hydrogen peroxide | 5 g |
| Orthophosphoric acid, q.s.p. | pH 3 |
| Water q.s.p. | 100 cc |

This lotion is applied to natural blond hair. After setting and drying, the hair is brightened and presents an ash pearly blond shade.

EXAMPLE 30

The following dyeing composition suitable for packaging in an aerosol container is prepared:

| | |
|---|---|
| Dye of Example 4 | 0.03 g |
| Dye of Example 1 | 0.1 g |
| Vinyl pyrrolidone-vinyl acetate copolymer (vinyl pyrrolidone — 60%, vinyl acetate — 40%, molecular weight 45,000– | |

| | |
|---|---|
| 60,000) | 3 g |
| Ethyl alcohol, 96° titer, q.s.p. | 100 cc |

This composition, packaged in an aerosol container with dichlorodifluoromethane as the propellant and sprayed in the form of a lacquer gives natural blend hair luminous golden glints.

EXAMPLE 31

The following hair-setting lotion is prepared:

| | |
|---|---|
| Dye of Example 11 | 0.005 g |
| Dye of Example 1 | 0.01 g |
| Dye of Example 8 | 0.001 g |
| Vinyl pyrrolidone-vinyl acetate copolymer (Vinyl pyrrolidone — 60%, vinyl acetate — 40%, molecular weight — 45,000–60,000) | 2 g |
| Ethyl alcohol, 96° titer | 50 cc |
| Triethanolamine, q.s.p. | pH 7 |
| Water, q.s.p. | 100 cc |

This hair-setting lotion when applied to freshly bleached hair, imparts thereto a light silvery shade.

EXAMPLE 32

The following dyeing composition is prepared:

| | |
|---|---|
| Dye of Example 17 | 0.096 g |
| Butylcellosolve | 8 g |
| Propylene glycol | 8 g |
| Alkyl phenol polyethoxyether sold under the name "Remcopal 334" by the Gerland company | 22 g |
| Alkylphenol polyethoxyether sold under the name "Remcopal 349" by the Gerland company | 22 g |
| Ammonia at 22° Bé | 8 g |
| Water, q.s.p. | 100 g |

20 g of 20 volume hydrogen peroxide is added to 20 g of the solution thus prepared and the gel thus obtained which, applied to ambient temperatures to bleached hair for 10 minutes, imparts to the hair a beige pearly shade.

EXAMPLE 33

The following dyeing composition is prepared:

| | |
|---|---|
| Dye of Example 17 | 0.2 g |
| Butylcellosolve | 8 g |
| Propylene glycol | 8 g |
| Alkylphenol polyethoxyether sold under the name "Remcopal 334" by the Gerland company | 22 g |
| Alkylphenol polyethoxyether sold under the name "Remcopal 349" by the Gerland company | 22 g |
| Ammonia at 22° Bé | 10 g |
| Water, q.s.p. | 100 g |

20 g of water are added to 20 g of the solution thus prepared. A gel is obtained which, applied to brown hair at ambient temperature for 15 minutes, imparts to the hair, after rinsing, a dark auburn brown shade.

EXAMPLE 34

The following dyeing composition is prepared:

| | |
|---|---|
| Dye of Example 8 | 0.050 g |
| Butylcellosolve | 8 g |
| Propylene glycol | 8 g |
| Alkylphenol polyethoxyether sold under the name "Remcopal 334" by the Gerland company | 22 g |
| Alkylphenol polyethoxyether sold under the name "Remcopal 349" by the Gerland company | 22 g |
| Water, q.s.p. | 100 g |

20 g of water are added to 20 g of the solution thus prepared. A gel is obtained which, applied at ambient temperature for 10 minutes to previously bleached hair, imparts to the hair an iridescent blond shade.

EXAMPLE 35

The following hair-setting lotion is prepared:

| | |
|---|---|
| Dye of Example 20 | 0.010 g |
| Vinyl pyrrolidone-vinyl acetate copolymer (vinyl pyrrolidone — 60%, vinyl acetate — 40%, molecular weight — 45,000–60,000) | 2.0 g |
| Ethyl alcohol, 96° titer | 50 cc |
| Triethanolamine, q.s.p. | pH 7 |
| Water, q.s.p. | 100 cc |

This hair-setting lotion when applied to hair dyed blond, imparts thereto a golden glint.

EXAMPLE 36

The following hair-setting composition is prepared:

| | |
|---|---|
| Dye of Example 22 | 0.012 g |
| Vinyl pyrrolidone-vinyl acetate copolymer (vinyl pyrrolidone — 60%, vinyl acetate — 40%, molecular weight, 45,000–60,000) | 2.0 g |
| Ethyl alcohol, 96° titer | 50 cc |
| Triethanolamine, q.s.p. | pH 7 |
| Water, q.s.p. | 100 g |

This hair-setting lotion when applied to bleached hair, imparts thereto a particularly luminous golden pink blond shade.

EXAMPLE 37

The following hair-setting lotion is prepared:

| | |
|---|---|
| Dye of Example 24 | 0.010 g |
| Vinyl pyrrolidone-vinyl acetate copolymer (vinyl pyrrolidone — 70%, vinyl acetate — 30%, molecular weight 35,000–45,000) | 2.0 g |
| Ethyl alcohol, 96° titer | 50 cc |
| Triethanolamine, q.s.p. | pH 7 |
| Water, q.s.p. | 100 cc |

This hair-setting lotion when applied to hair dyed golden blond, imparts thereto a luminous and aesthetic pearl glint.

EXAMPLE 38

The following hair-setting lotion is prepared:

| | |
|---|---|
| Dye of Example 23 | 0.015 g |
| Vinyl pyrrolidone-vinyl acetate copolymer (vinyl pyrrolidone — 70%, vinyl acetate — 30%, molecular weight 35,000–45,000) | 2.0 g |
| Ethyl alcohol, 96° titer | 50 cc |

| | |
|---|---|
| Triethanolamine, q.s.p. | pH 8 |
| Water, q.s.p. | 100 cc |

This hair-setting lotion when applied to bleached hair, imparts thereto a very luminous light pink blond shade.

EXAMPLE 39

The following hair-setting lotion is prepared:

| | |
|---|---|
| Dye of Example 7 | 0.70 g |
| Vinyl acetate-crotonic acid copolymer (vinyl acetate — 90%, crotonic acid — 10%, molcular weight, 45,000–50,000) | 2.0 g |
| Ethyl alcohol, 96° titer | 50 cc |
| Benzylidene camphor | 0.2 g |
| Triethanolamine, q.s.p. | pH 7 |

This hair-setting lotion when applied to hair dyed dark blond, imparts thereto a luminous pearl ash glint.

EXAMPLE 40

The following hair-setting lotion is prepared:

| | |
|---|---|
| Dye of Example 22 | 0.010 g |
| Vinyl prrolidone-vinyl acetate copolymer (vinyl pyrrolidone — 70%, vinyl acetate — 30%, molecular weight 35,000–45,000) | 2.0 g |
| Ethyl alcohol, 96° titer | 50 cc |
| Triethanolamine, q.s.p. | pH 7 |
| N-[(4'-amino 2'-methoxy 3',5'-dimethyl) phenyl] 2,5-dimethyl benzoquinoneimine | 0.010 g |
| Water, q.s.p. | 100 cc |

This hair-setting lotion, when applied to light blond hair, imparts thereto a pearl ash shade.

EXAMPLE 41

The following dyeing composition is prepared:

| | |
|---|---|
| Dye of Example 24 | 0.012 g |
| N-[(4'-hydroxy)phenyl] 3-amino- 6-methyl benzoquinoneimine | 0.010 g |
| N-[(4'-amino 2'-methoxy 3',5'-dimethyl) phenyl] 2,6-dimethyl benzoquinoneimine | 0.002 g |
| Ethyl alcohol, 96° titer | 50 cc |
| Water, q.s.p. | 100 cc |

This dye composition when applied to strongly bleached hair for 20 minutes at ambient temperature, imparts thereto after rinsing and shampooing, a golden apricot shade.

EXAMPLE 42

The following hair-setting composition is prepared:

| | |
|---|---|
| Dye of Example 20 | 0.005 g |
| Dye of Example 24 | 0.005 g |
| N-[(4'-hydroxy)phenyl]3-amino 6-methyl benzoquinoneimine | 0.0025 g |
| N-[(4'-amino 2'-methoxy 3',5'-dimethyl) phenyl]2,5-dimethyl benzoquinoneimine | 0.001 g |
| Vinyl pyrrolidone-vinyl acetate copolymer (vinyl pyrrolidone — 70%, vinyl acetate — 30%, molecular weight 35,000–45,000) | 2.0 g |
| Triethanolamine, q.s.p. | pH 7 |
| Water, q.s.p. | 100 cc |

This hair-setting lotion when applied to blond hair imparts thereto a pearly glint.

EXAMPLE 43

The following setting lotion is prepared:

| | |
|---|---|
| Dye of Example 24 | 0.006 g |
| Dye of Example 22 | 0.004 g |
| N-[(4'-hydroxy)phenyl] 3-amino 6-methyl benzoquinoneimine | 0.001 g |
| N-[(4'-amino 2'-methoxy 5'-methyl)phenyl] 3-acetylamino 6-methyl benzoquinoneimine | 0.005 g |
| Vinylpyrrolidone-vinyl acetate copolymer (vinyl pyrrolidone — 60%, vinyl acetae — 40%, molecular weight — 45,000-60,000) | 2.0 g |
| Ethyl alcohol, 96° titer | 50 cc |
| Triethanolamine, q.s.p. | pH 7 |
| Benzylidene camphor | 0.2 g |
| Water, q.s.p. | 100 cc |

This hair-setting lotion when applied to very light natural blond hair, imparts thereto a luminous ash pearl glint.

EXAMPLE 44

The following hair-setting lotion is prepared:

| | |
|---|---|
| Dye of Example 23 | 0.007 g |
| N-(4'-amino 2'-methoxy 3',5'-dimethyl) phenyl 2,5-dimethyl benzoquinoneimine | 0.003 g |
| N-(4'-hydroxy)phenyl 2,6-dimethyl benzoquinoneimine | 0.003 g |
| Vinyl pyrrolidone-vinyl acetate copolymer (vinyl pyrrolidone — 60%, vinyl acetate — 40%, molecular weight 45,000-60,000) | 2.0 g |
| Ethyl alcohol, 96° titer | 50 cc |
| Triethanolamine, q.s.p. | pH 6 |
| Water, q.s.p. | 100 cc |

This hair-setting lotion when applied to hair dyed light blond, imparts thereto ash pearl glints.

EXAMPLE 45

The following hair-setting lotion is prepared:

| | |
|---|---|
| Dye of Example 22 | 0.010 g |
| Nitroparaphenylenediamine | 0.010 g |
| Vinyl pyrrolidone-vinyl acetate copolymer (vinyl pyrrolidone — 60%, vinyl acetate — 40%, molecular weight 45,000-60,000) | 2.0 g |
| Ethyl alcohol, 96° titer | 60 cc |
| Triethanolamine, q.s.p. | pH 9 |
| Water, q.s.p. | 100 cc |

This hair-setting lotion when applied to hair dyed light brown, imparts thereto golden copper glints.

EXAMPLE 46

The following dyeing composition is prepared:

| | |
|---|---|
| Dye of Example 22 | 0.010 g |
| Dye of Example 23 | 0.010 g |
| 4-methyl di-β-hydroxymethylamino-8(2,3-b) morpholino phenoxazonium bromide | 0.010 g |
| Crotonic acid-vinyl acetate copolymer (crotonic acid — 10%, vinyl acetate — 90%, molecular weight 45,000-50,000) | 2.0 g |
| Ethyl alcohol, 96° titer | 50 cc |
| Triethanolamine, q.s.p. | pH 6 |

| Water, q.s.p. | 100 cc |
|---|---|

This hair-setting lotion when applied to hair bleached and dyed dark brown imparts thereto a luminous bluish ash glint.

As used in the preceding examples, "Remcopal 334" is a nonylphenol polyethoxyether obtained by condensation of 4 moles of ethylene-oxide with 1 mole of nonylphenol, and "Remcopal 349" is a nonylphenol polyethoxyether obtained by condensation of 9 moles of ethylene-oxide with 1 mole of nonylphenol. Both are commercially available from the Gerland company.

EXAMPLE 47

Preparation of 1'-(4'-N,N-dimethylamine benzene) 2-azo 1-methylpyridinium methyl sulfate.

(A) preparation of 1'-(4-N,N-dimethylamino benzene) 2-azo pyridine-N-oxide of the formula

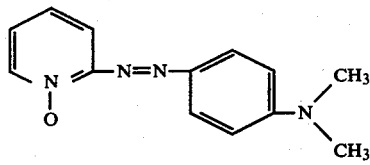

A solution of 0.1 mole of the chloride of N-oxy pyridyl-2 diazonium (prepared according to the method of Katritzky, Journal of the Chemical Society, 1957, P. 191) which was cooled and maintained at 0° C. was added slowly to a solution of 12.1 g of N,N-dimethylaniline in 12 cm³ acetic acid.

The mixture is agitated for 30 minutes; subsequently adding two portions of 40 cm³ of a 40% aqueous solution of sodium acetate. The precipitate produced thereby is filtered, washed with water and dried. After recrystallizing the precipitate from a 50% alcohol-water solvent, a product is obtained which has a melting point of 188° C.

Elemental Analysis: $C_{13}H_{14}N_4O$; Theoretical: % C 64.45, H 5.79, N 23.15; Actual: % C 64.25, H 6.11, N 22.95.

(B) Preparation of the methylsulfate salt of 1'-(4'-N,N-dimethylamino benzene) 2-azo 1-methoxy pyridine of the formula

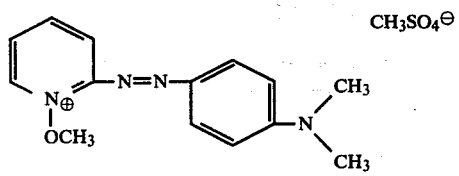

0.1 mole of the product of Step (A) is suspended in 100 cm² N-methyl pyrrididone-2. 35 cm³ of dimethyl sulfate is added dropwise to the suspension with constant stirring; stirring is continued for an additional hour. The precipitate which forms is filtered, washed with 35 cm³ acetone and recrystallized from alcohol (ethanol).

The isolated product has a melting point of 197° C.

Elemental Analysis: $C_{15}H_{20}N_4O_5S$; Theoretical: % C 48.90; H 5.43, N 15.22; Experimental: % C 49.08, H 5.62, N 15.10.

(C) Preparation of 1'-(4'-dimethylamino benzene) 2-azo pyridine of the formula

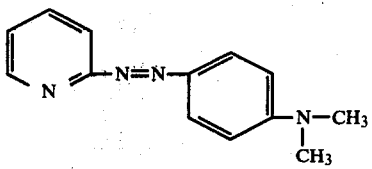

0.1 mole of the product obtained in Step (B) is dissolved in 600 cm³ of 90% alcohol and 42 cm³ ammonia. The solution is heated for one hour at reflux and then the solvent is distilled off under reduced pressure. The residue is mixed with 100 cm³ of water and is filtered. After recrystallizing the residue from cyclohexane, the product has a melting point of 112° C.

Elemental Analysis of the compound resulted in an emperical formula: $C_{13}H_{14}N_4O$; Theoretical: % C 69.00, H 6.2, H 24.8; Experimental: % 69.03, H 5.93, N 25.06.

(D) Preparation of methylsulfate of 1'(4'-N,N-dimethylamino benzene) 2-azo 1-methyl pyridinium

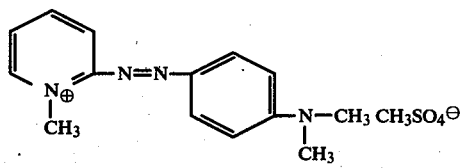

0.1 mole of the compound produced in (C) above was dissolved in 100 cm³ of N-methyl pyrrolidone-2. While the solution was stirred vigorously, 19.5 cm³ of dimethyl sulfate was added dropwise to the solution of the compound of (C). The solution was stirred for one hour, then filtered, washed with acetone and recrystallized from alcohol.

The product obtained has a melting point of 210° C. and on elemental analysis an empirical formula was determined: $C_{15}H_{20}N_4O_4S$; Theoretical: % C 51.12, H 5.68, N 15.95; Actual: % C 51.12, H 5.77, N 16.04.

EXAMPLE 48

Preparation of methylsulfate of 1'-(4'-diethylamino benzene) 2-azo 1-methyl pyridinium of the formula:

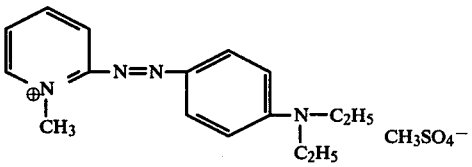

The process for obtaining this compound was similar to the process in Example 47, with the exception that N,N-diethylaniline was employed; rather than N,N-dimethylaniline. The product had a melting point of 129° C. and an empirical formula $C_{17}H_{24}N_4O_4S$ on elemental analysis (Theoretical percentages: C 53.70; H 6.32; and N 14.73. Actual percentages: C 53.34; H 6.49; and N 14.72).

EXAMPLE 49

Preparation of the methylsulfate of 1'-(4'-dimethylamino benzene) 2-azo 1,3-dimethyl pyridinium of the formula

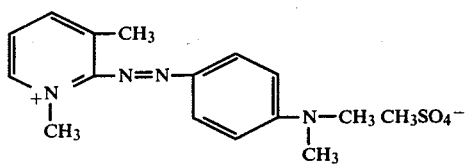

The procedure for preparing this compound was similar to that in Example 47, except that the diazotized amine is 2-amino-3-methyl pyridine-N-oxide. The melting point at the product was 210° C. The empirical formula for this product was $C_{16}H_{22}N_4O_4$, based on 52.47 percent C, 6.16 H and 15.11 N. (Theoretical: percent C 52.44; H 6.01 and N 15.30).

EXAMPLE 50

Preparation of the methyl sulfate of 1'-(4'-bis (β-hydroxyethyl) amino benzene) 2-azo 1,4-dimethyl pyridinium of the formula

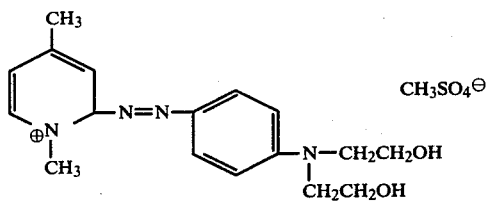

The product of the formula is prepared according to the process of Example 47, with the exception that the diazonium compound used in Example 50 in (A) was 2-amino-4-methyl-pyridine N-oxide and the aniline derivative was N,N(β-hydroxyethyl) aniline. On recrystallization from alcohol, the product obtained had a melting point of 165° C., and the empirical formula, based on elemental analysis of the product was $C_{18}H_{26}N_4O_6S$. (Theoretical: 50.70% C, 6.10% H and 13.13% N, while experimental evidence yielded 50.73% C, 6.11% H and 13.27% N.

EXAMPLE 51

Preparation of the methyl sulfate of 1'-(4'-dimethyl amino 2'-methyl benzene) 2-azo 5-chloro 1-methyl of the formula:

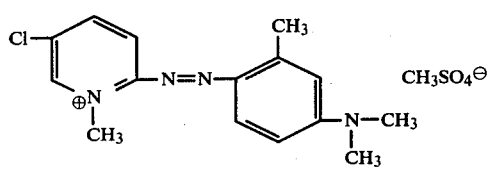

The procedure for producing this compound was similar to the procedures set forth in Example 47, with the exception that the chloride of N-oxypyridyl-2-chloro-5-diazonium and 3-methyl-N,N-dimethylaniline were used in Step A. The melting point of the product was 242° C.

EXAMPLE 52

Preparation of the methyl sulfate salt of 1'-(4'amino benzene) 2-azo 1-methyl-1-pyridinium.

(A) Preparation of the sodium salt of the 1'oxy-pyridine azo-2':4-anilino methylsulfonate of the formula:

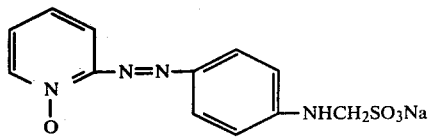

0.11 moles of the ω-sodium salt of N-anilino methyl sulfonic acid was dissolved in 17 cm³ of water. 53 grams of crystalline sodium acetate was then added and the solution was cooled to 5° C. The 0.1 mole of N-oxypyridyl-2-diazonium chloride, prepared according to Katritzki, Journal of the Chemical Society, 1957, page 191, was added slowly to the cold solution. Subsequently, 130 grams of crystalline sodium acetate was added and was allowed to react in the solution for approximately 1 hour. The product was isolated by filtration and was dried over phosphoric anhydride. The product when crystallized from water had a melting point of 160° C. The empirical formula for the product, based on elemental analysis was $C_{12}H_{11}N_4O_4SNa, 3H_2O$. (Theoretical calculation: 37.50% C, 4.32% H and 14.55% N, while experimental percentages were 37.99% C, 3.46% H and 14.26% N).

(B) Preparation of 1'-(4'-amino-benzene) 2-azo pyridine-N-oxide, of the formula:

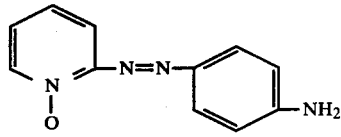

0.1 moles of the composition realized in Step A was dissolved in 200 cm³ of a 10% ammonical solution and heated for 5 hours at 60° C. The solution and mixture was allowed to cool, was then filtered, was washed with water and dried. The product, recrystallized from methanol, had a melting point of 300° C. The empirical formula derived from an elemental analysis, was $C_{11}H_{10}N_4O$; (theoretical calculation: 61.70% carbon, 4.67% hydrogen and 26.17% nitrogen, while elemental analysis indicated 61.79% carbon, 4.93% hydrogen and 25.99% nitrogen.

(C) Preparation of 1'-(4'-amino-benzine) 2-azo 1-methoxypyridinium methyl sulfate of the formula:

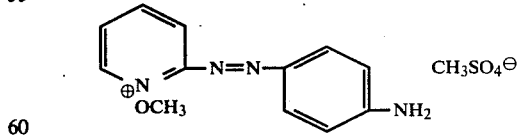

0.1 mole of the product produced in Step B was dissolved in 100 cm³ of N-methylpyrrolidone-2. 12.5 cm³ of dimethyl sulfate was added dropwise to the solution and allowed to react over night. The dye was precipitated by adding ethyl acetate. On filtering, the precipitate was washed with alcohol and then with ether and then dried.

(D) Preparation of 1'-(4'-aminobenzene) 2-azo pyridine of the formula:

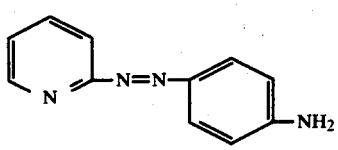

0.1 mole of the product produced in Step C was dissolved in 600 cm$^3$ of 90% ethyl alcohol and 42 cm$^3$ of concentrated ammonia and then heated to reflux for 1 hour. The solvent was distilled under reduced pressure and the product was recrystallized in ethyl acetate.

(E) Preparation of 1'-(4'-amino-benzene) 2-azo 1-methylpyridinium methyl sulfate, of the formula:

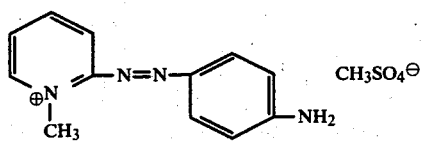

0.1 mole of the product obtained in Step D was dissolved in 100 cm$^3$ N-methyl-pyrrolidone-2. 12.5 cm$^3$ of dimethyl sulfate was added to the solution, with stirring, and then the solution was allowed to act for approximately 1 hour and 30 minutes. Thereafter 400 cm$^3$ of ethyl acetate was added to the solution; the oil which was produced was decanted and the oil was recrystallized from absolute alochol. The product had a melting point of 193° C. On elemental analysis, the product produced in Step E was found to contain 48.28% C, 5.00% H and 17.21% N, while theoretical calculations would have resulted in a compound containing 48.15% C, 4.94% H and 17.29% N.

EXAMPLE 53

Preparation of 1'-(4'-amino-benzene) 2-azo 1,3-dimethylpyridinium methyl sulfate of the formula:

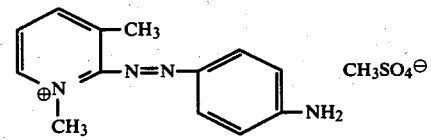

This composition was obtained according to the procedure described in Example 52, by employing 2-amino 3-methyl pyridine N-oxide as the diazotized amine. After recrystallization from absolute ethyl alcohol, the product had a melting point of 183° C. The empirical formula based on elemental analysis was $C_{14}H_{18}N_4O_4S$. Theoretical calculations would have resulted in a compound containing 49.70% C, 5.33% H and 16.56% N, while elemental analysis showed 49.54% C, 5.35% H and 16.35% N.

EXAMPLE 54

Preparation of 1'-(4'-amino 8'-hydroxy naphthalene) 2-azo 1-methyl pyridinium methyl sulfate.

(A) Preparation of 1'-(4'-amino 8'hydroxy naphthalene) 2-azo pyridine N-oxide, of the formula:

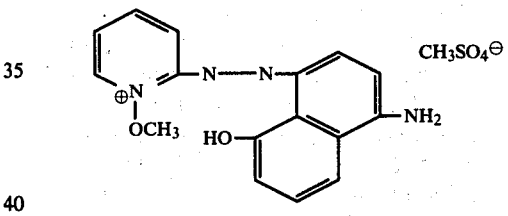

A solution of 0.1 mole of N-oxy-pyridyl-2 diazonium chloride, maintained at 0° C., prepared according to Katritsky, Journal of the Chemical Society, 1957, page 191, was added to a solution of 5-acetoxy naphthalamine-1 monochloro hydrate in 900 cm$^3$ of 80% acetic acid, which was maintained at 5° C. throughout the addition. The reaction mixture was maintained at a pH of 4 by the addition of sodium acetate. Thereafter, 1.5 liters of water was added over a period of 30 minutes, the product was filtered and then dried. The product obtained was dissolved in 450 cm$^3$ of 2-methoxyethanol. Then, 150 cm$^3$ of aqueous hydroxide was added to the solution and the solution was stirred for 30 minutes. Then 3 liters of water were added, the solution was neutralized with acetic acid and dried. The product had a melting point of 280° C.

(B) Preparation of 1'-(4'-amino 8'hydroxy naphthalene) 2-azo 1-methoxy pyridinium methyl sulfate of the formula:

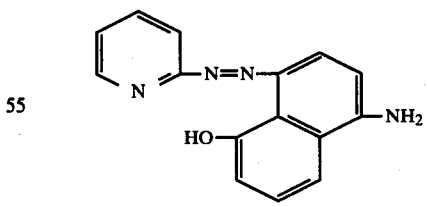

0.1 moles of the product produced in Step A is dissolved in 125 cm$^3$ N-methyl pyrrolidone-2 and then 15 cm$^3$ of dimethyl sulfate was added dropwise to the solution. Stirring was continued throughout the reaction. The product was filtered after adding ethyl acetate to the reaction mixture.

(C) Preparation of 1'-(4'-amino 8'hydroxy naphthalene) 2-azo pyridine, of the formula:

0.1 mole of the product of Step B was dissolved in 1 liter of 90% ethyl alcohol and 100 cm$^3$ of concentrated ammonia. The solution was heated to reflux for an hour and then evaporated to dryness. The product was mixed with water, filtered and dried.

(D) Preparation of 1'-(4'-amino 8'-hydroxy naphthalene) 2-azo 1-methyl pyridinium methyl sulfate of the formula:

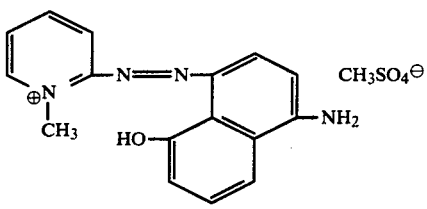

0.1 mole of the product of Step C was dissolved in 125 cm³ N-methyl pyrrolidone-2. While stirring, 15 cm³ of methyl sulfate was added dropwise to the solution and the reaction mixture was stirred until the reaction was complete. The product was precipitated by the addition of ethyl acetate. The product had a melting point of 250° C.

EXAMPLE 55

Preparation of 1'-(4'-N,N-dimethylamino benzene) 2-azo 4-cyano 1-methyl pyridinium methyl sulfate.

(A) Preparation of 1'-(4'-dimethylamino benzene) 2-azo 4-cyano pyridine, of the formula:

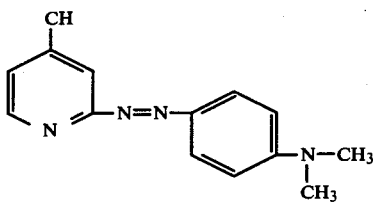

0.1 mole of the product of Step H of Example 47 was dissolved in 40 cm³ of water to form a solution. Then, with stirring, 10 grams of sodium cyanide in 50 cm³ of water was added dropwise to the solution. The solution was heated to 80° C. for 3 hours, allowed to cool, and then filtered. The product was recrystallized from chloroform and had a melting point of 190° C. The empirical formula resulting from elemental analysis was $C_{14}H_{13}N_5$. Theoretical calculations would have resulted in a compound containing 66.95% carbon, 5.18% hydrogen, and 27.87% nitrogen. In fact, elemental analysis of the product indicated 66.81% carbon, 5.18% hydrogen and 27.78% nitrogen.

(B) Preparation of 1'-(4'-dimethylamino benzene) 2-azo 4-cyano 1-methyl pyridinium methyl sulfate, of the formula:

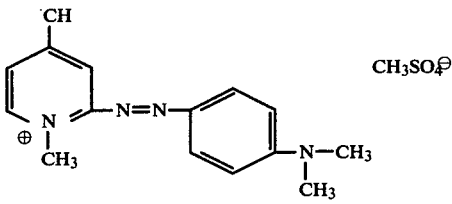

0.1 mole of the product of Step A above was dissolved in 300 cm³ of N-methyl pyrrolidone-2. 15 cm³ of dimethyl sulfate was added dropwise to the solution. The solution was heated to 50° C. until reaction was complete. The product was precipitated by the addition of ethyl acetate and purified by chromotography on a silicagel column. The product had a melting point of 208° C.

EXAMPLE 56

Preparation of 1'-(2'-chloro 4'-N,N-dimethylamino benzene) 2-azo 1-methyl pyridinium methyl sulfate.

(A) Preparation of 1'-(2'-chloro 4'-N,N-dimethylamino benzene) 2-azo pyridine N-oxide of the formula:

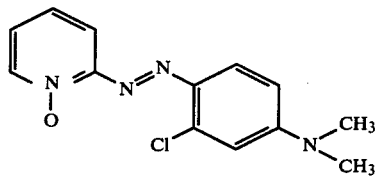

5 grams (0.032 mole) of meta-chloro N,N-dimethyl aniline was dissolved in 6 cm³ of acetic acid and the solution was cooled to 5° C. Thereafter, to this solution was added slowly a solution of the diazonium salt prepared as in Example 47 from 0.032 mole of amino-2 pyridine N-oxide. The precipitate obtained was suspended in water; a saturated solution of sodium bicarbonate was then added to the suspension to neutralize the suspension. The solid was isolated, dried and recrystallized from ethyl alcohol and had a melting point of 202° C.

(B) Preparation of 1'-(2'-chloro 4'-dimethylamino benzene) 2-azo pyridinium methyl sulfate:

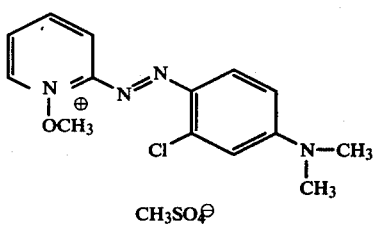

4.45 grams of the product produced in Step A was dissolved in 11.15 cm³ of N-methyl pyrrolidone; while stirring that solution, 1.7 cm³ of dimethyl sulfate was added dropwise to the solution. Stirring of the solution was continued for 1 hour. The precipitate formed was filtered and washed with acetone.

(C) Preparation of 1'-(2'-chloro 4'-dimethylamino benzene) 2-azo pyridine:

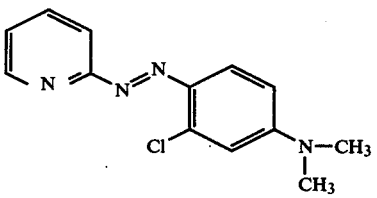

5 cm³ of concentrated ammonia was added to a solution of 4.75 grams of the product produced in Step B dissolved in 73 cm³ of 90% ethanol. The solution was heated to reflux until the reaction was complete. The solution was then concentrated to dryness under reduced pressure, and the reaction product was purified by chromotography on a silicagel column, employing ethyl acetate as an eluent.

(D) Preparation of 1'-(2'-chloro 4'-dimethylamino benzene) 2-azo 1-methyl pyridinium methyl sulfate:

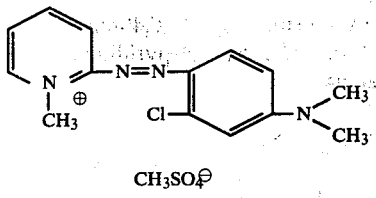

3 grams of the product of Step C was dissolved in 7 cm³ of H-methyl pyrrolidone and, during vigorous stirring, 1.2 cm³ of dimethyl sulfate was added slowly to the solution. Stirring of the solution was maintained for approximately an hour after a precipitate formed. The precipitate was washed with ethyl acetate and dried. The product dye was purified by recrystallization in ethanol. The melting point of the product was 225° C. The empirical formula based on elemental analysis for the product was $C_{15}H_{19}N_4O_4SCl$. Theoretical calculations would have resulted in a product containing 14.48% nitrogen, while elemental analysis proved that the product contained 14.72–14.41% nitrogen.

EXAMPLE 57

Preparation of 1'-[2'-acetylamino 4'-N,N-dimethylamino benzene] 2-azo 1-methyl pyridinium methyl sulfate of the formula

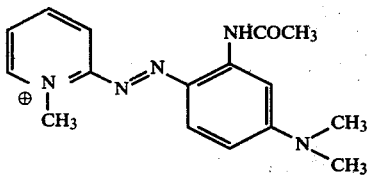

The aforementioned composition was obtained in accordance with procedures identical to those of Example 47, wherein the only difference was that in Step A, a solution of metaacetylamino N,N-dimethylaniline was substituted as the aniline compound. The product had a melting point of 222° C. after recrystallization from methanol.

Elemental Analysis: $C_{17}H_{23}N_5O_5S$; Theoretical: % C 49.89, H 5.62, N 17.11; Experimental % C 49.66, H 5.45, N 17.31.

EXAMPLE 58

Preparation of 1'-[2'-nitro 4'-dimethylamino benzene] 2-azo 1-methyl pyridinium methyl sulfate of the formula

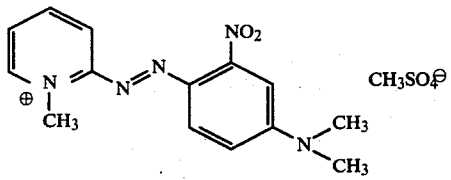

This composition was prepared in accordance with the procedures of Example 47 except that in Step A, a solution of meta-nitro N,N-dimethylaniline was substituted. The product obtained had a melting point of 254° C. after recrystallization from methanol.

Elemental Analysis: $C_{15}H_{19}N_5O_6S$, ½ $CH_3OH$; Theoretical: % C 45.00, H 5.08, N 16.94; Experimental: % C 44.81, H 5.33, N 17.08.

EXAMPLE 59

Preparation of 1'-[4'-amino 3'-methoxy benzene] 2-azo 1-methyl pyridinium methyl sulfate of the formula

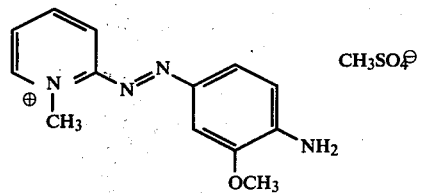

This composition was obtained in accordance with the procedures described in Example 47, with the exception that orthoanisidine was substituted as a reactant in Step A. After recrystallization from ethyl alcohol, the product had a melting point of 205° C.

Elemental Analysis: $C_{14}H_{18}N_4O_5S$; Theoretical: % C 47.50, H 5.08, N 15.82; Experimental: % C 47.28, H 5.28, N 15.72.

EXAMPLE 60

Preparation of 1'-[2',4'-diamino 5'-methyl benzene] 2-azo 1,5-dimethyl pyridinium methyl sulfate.

(A) Preparation of 1'-[2',4'-diamino 5'-methyl benzene] 2-azo 5-methyl pyridinium N-oxide of the formula

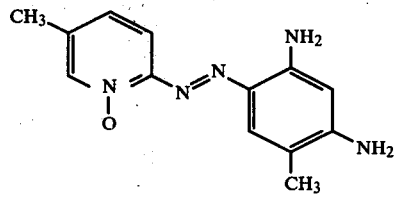

A solution of 0.1 mole of the chloride of 5-methyl N-oxypyridyl-2 diazonium (prepared in accordance with Katrizky, *Journal of the Chemical Society* 1957, page 191) was cooled to 0° C. and then added slowly to a solution of 12.2 grams of 2,4-diamino toluene dissolved in 20 cm³ of acetic acid, which was maintained at 5° C. throughout the addition.

Stirring of the solution was continued for 30 minutes and then 34 grams of crystalline sodium acetate was added. The precipitate was filtered, washed with water and then dried.

(B) Preparation of 1'-[2',4'-diacetylamino 5'-methyl benzene] 2-azo 5-methyl pyridine N-oxide of the formula

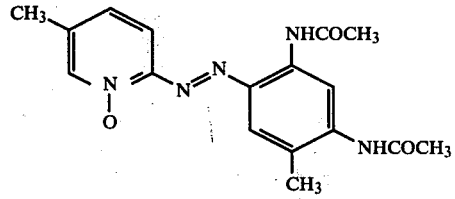

0.1 mole of the product obtained in Step A above was dissolved in 300 cm³ of acetic acid. 88 grams of acetic anhydride was added stepwise to that solution and heated for two hours on a boiling water bath. The mixture was allowed to cool; and then the reaction mixture was poured over 500 grams of ice. The solution which was obtained was neutralized with sodium carbonate. The precipitate which resulted was filtered, washed with water and dried.

(C) Preparation of 1'-[2',4'-diacetylamino 5'-methyl benzene] 2-azo 1-methoxy 5-methyl pyridinium methyl sulfate of the formula

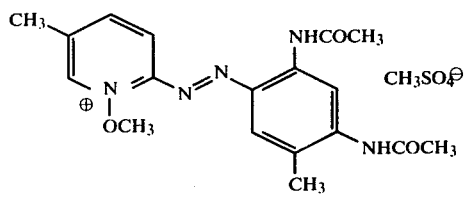

0.1 mole of the product obtained in Step B above, was dissolved in 160 cm³ of N-methyl pyrrolidone-2. 9 cm³ of dimethyl sulfate was added dropwise to the solution of the product of Step B with continual and vigorous stirring. The reaction mixture was allowed to react overnight and then an additional 2 cm³ of dimethyl sulfate was added to the reaction mixture. The precipitate which was obtained was filtered, washed with acetone and then dried.

(D) Preparation of 1'-[2',4'-diacetylamino 5'-methyl benzene] 2-azo 5-methyl pyridine of the formula

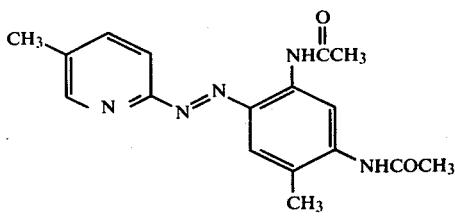

0.1 mole of the product obtained in Step C above was dissolved in 2300 cm³ of 90% ethyl alcohol. 190 cm³ of concentrated ammonia was added to the alcohol solution and then the solution was stirred for 45 minutes at ambient temperatures. The solvent was distilled from the mixture under reduced pressure. The residue was mixed with 100 cm³ of water, filtered and dried.

(E) Preparation of 1'-[2',4'-diamino 5'-methyl benzene] 2-azo 5-methyl pyridine of the formula

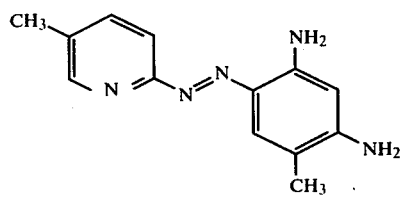

0.1 mole of the product of Step D was dissolved in 100 cm³ of 5 normal hydrochloric acid and was then heated at reflux for 3 hours. The reaction mixture was allowed to cool and neutralized by the addition of sodium bicarbonate. The reaction mixture was extracted with chloroform. The solvent was then distilled under reduced pressure. The product was purified by chromatography on a silicagel, employing dichloroethane as an eluent.

(F) Preparation of 1'-[2',4'-diamino 5'-methyl benzene] 2-azo 1,5-dimethyl pyridinium methyl sulfate of the formula

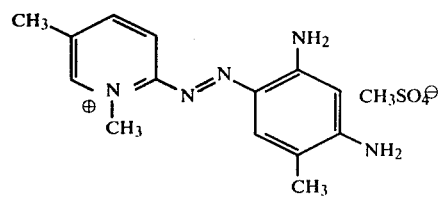

0.1 mole of the product obtained in Step E was dissolved in 7500 cm³ of dichloroethane. 10 cm³ of dimethyl sulfate was added dropwise to the solution of the product of Step E, while stirring the mixture, during addition and for 30 minutes following addition. The product obtained was filtered and recrystallized from ethyl alcohol. The product had a melting point of 252° C.

Elemental Analysis: $C_{15}H_{21}N_5O_4S$; Theoretical: % C 49.08, H 5.72, N 19.04; Experimental: % C 48.78, H 5.88, N 19.28.

EXAMPLE 61

Preparation of 1'-[4'-bis (β-hydroxyethyl) amino benzene] 2-azo 6-cyano 1,4-dimethyl pyridinium perchlorate of the formula

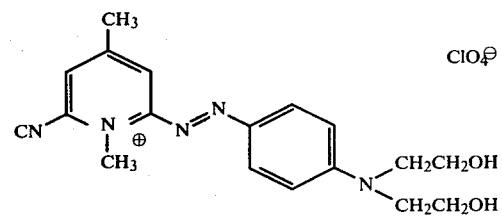

This composition was obtained in accordance with the procedures set forth in Example 9, except that a solution of 1'-[4'-bis (β-hydroxyethyl) amino benzene] 2-azo 1-methoxy 4-methyl pyridinium methyl sulfate was used in Step A. The product produced was purified by washing with water and then with an aqueous solution of sodium perchlorate. The product had a melting point of 210° C., with the composition.

EXAMPLE 62

Preparation of 1'-[4'-phenylamino benzene] 2-azo 1,6 dimethyl pyridinium methyl sulfate of the formula

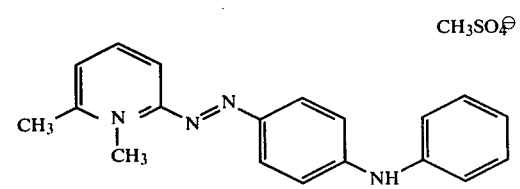

This composition was obtained in accordance with Example 47, with the exception that the chloride of 6-methyl N-oxypyridyl-2 diazonium and diphenylamine were used in Step A. On recrystallization from methanol, the product had a melting point of 220° to 222° C.

Elemental Analysis: $C_{17}H_{23}N_5O_5S$; Theoretical: % C 49.89, H 5.62, N 17.11; Experimental: % C 49.66, H 5.45, N 17.31.

The 1′-[4′-dimethylamino benzene] 2-azo 1,5 dimethyl pyridinium methyl sulfate of the formula

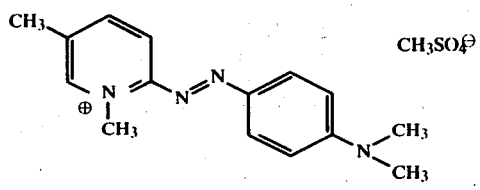

has a melting point of 168° C. on recrystallization from ethyl alcohol.

Elemental Analysis: $C_{16}H_{22}N_4O_4S$; Theoretical: % C 52.58, H 6.01, N 15.30; Experimental: % C 52.18, H 6.07, N 15.22.

Prepared in accordance with classical methods, this compound may be utilized in compositions described below.

EXAMPLE A

A dye composition was prepared by mixing

| | |
|---|---|
| Dye of Example 47 | 0.050 g |
| Copolymer of vinylacetate-crotonic aci (90/10) | 1.8 g |
| Copolymer of vinylacetate-vinylpyrrolidone (40/60) | 0.3 g |
| Ethyl alcohol 50° titer | |
| Triethanolamine q.s.p. pH 9 | |
| Water, q.s.p. | 100 cc. |

When applied to natural chestnut color hair, the above composition imparts thereto violet hues and glints.

EXAMPLE B

A composition was prepared by mixing

| | |
|---|---|
| Dye of Example 48 | 0.030 g |
| A vinylacetate-crotonic acid copolymer (90/10) | 1.8 g |
| A vinylacetate-vinylpyrrolidone copolymer (40/60) | 0.3 g |
| Ethyl alcohol 50° titer | |
| triethanolamine q.s.p. pH 7 | |
| Water q.s.p. | 100 cc. |

When this lotion was applied to hair dyed chestnut color, it imparted to the hair glints of violet hue.

EXAMPLE C

A dye composition was prepared by mixing

| | |
|---|---|
| Dye of Example 52 | 0.050 g |
| A vinylacetate-crotonic acid copolymer (90/10) | 1.8 g |
| A vinylacetate-vinylpyrrolidone copolymer (40/60) | 0.3 g |
| Ethyl alcohol 50° titer | |
| Triethanolamine q.s.p. pH 7 | |
| Water q.s.p. | 100 cc. |

When applied to natural dark brown hair, it imparted thereto glints of mahogany color.

EXAMPLE D

A dye composition was prepared by mixing

| | |
|---|---|
| Dye of Example 54 | 0.050 g |
| Vinylacetate-crotonic acid copolymer (90/10) | 1.8 g |
| Vinylacetate-vinylpyrrolidone copolymer (40/60) | 0.3 g |
| Ethyl alcohol 50° titer | |
| Citric acid q.s.p. pH 5 | |
| Water q.s.p. | 100 cc. |

When applied to hair dyed deep blond, this composition imparted thereto glints of ash color.

EXAMPLE E

A dye composition was prepared by mixing

| | |
|---|---|
| Dye of Example 49 | 0.050 g |
| Vinylacetate-crotonic acid copolymer (90/10) | 1.8 g |
| Vinylacetate-vinylpyrrolidone (40/60) | 0.3 g |
| Ethyl alcohol 50° titer | |
| Triethanolamine q.s.p. pH 7 | |
| Water q.s.p. | 100 cc. |

When applied to hair dyed blond, this composition imparted red highlights thereto.

EXAMPLE F

A dye composition was prepared by mixing

| | |
|---|---|
| Dye of Example 53 | 0.050 g |
| Vinylacetate-crotonic acid copolymer (90/10) | 1.8 g |
| Vinylacetate-vinylpyrrolidone (40/60) | 0.3 g |
| Ethyl alcohol 50° titer | |
| Citric acid q.s.p. pH 5 | |
| Water q.s.p. | 100 cc. |

When applied to natural brown hair, this composition imparted to the hair red-orange highlights.

EXAMPLE G

A dye lotion was prepared by mixing

| | |
|---|---|
| Dye of Example 50 | 0.050 g |
| Vinylacetate-crotonic acid copolymer (90/10) | 1.8 g |
| Vinylacetate-vinylpyrrolidone (40/60) | 0.3 g |
| Ethyl alcohol 50° titer | |
| Triethanolamine q.s.p. pH 7 | |
| Water q.s.p. | 100 cc. |

When applied to natural brown hair, this lotion imparted to the hair violet highlights.

EXAMPLE H

The hair dye lotion of this Example was prepared by mixing

| | |
|---|---|
| Dye of Example 55 | 0.050 g |
| Vinylacetate-crotonic acid copolymer (90/10) | 1.8 g |
| Vinylacetate-vinylpyrrolidone copolymer (40/60) | 0.3 g |
| Ethyl alcohol q.s.p. 50° titer | |
| Triethanolamine q.s.p. pH 9 | |
| Water q.s.p. | 100 cc. |

When applied to hair dyed dark brown, it imparted to the hair iridescent ash colored highlights and overtones.

EXAMPLE I

The dye lotion of this Example was prepared by mixing

| | |
|---|---|
| Dye of Example 51 | 0.050 g |
| Vinylacetate-crotonic acid copolymer (90/10) | 1.8 g |
| Vinylacetate-vinylpyrrolidone copolymer(40/60) | 0.3 g |
| Ethyl alcohol q.s.p. 50° titer | |

Citric acid q.s.p. pH 5
Water q.s.p.   100 cc.

When applied to hair naturally dark brown, this composition imparted mauve-ash colored overtones and highlights.

EXAMPLE J

A dye composition was prepared by mixing

| | |
|---|---|
| Dye of Example 54 | 0.0312 g |
| Dye of Example 50 | 0.0187 g |
| Vinylacetate-crotonic acid copolymer (90/10) | 1.8 g |
| Vinylacetate-vinylpyrrolidone copolymer (40/60) | 0.3 g |
| Ethyl alcohol q.s.p. 50° titer | |
| Triethanolamine q.s.p. pH 7 | |
| Water q.s.p. | 100 cc. |

When applied to hair dyed brown, this lotion imparted to the hair ash-brown overtones.

EXAMPLE K

A dye composition was prepared by mixing

| | |
|---|---|
| Dye of Example 53 | 0.020 g |
| Dye of Example 55 | 0.025 g |
| Vinylacetate-crotonic acid copolymer (90/10) | 1.8 g |
| Ethyl alcohol q.s.p. 55° titer | |
| Water, oxygenated by 200 volumes | 5 cc. |
| Orthophosphoric acid q.s.p. pH 3 | |
| Water q.s.p. | 100 cc. |

When applied to hair naturally dark blond colored, this composition imparted lightness to the color of the hair, and violet colored highlights.

EXAMPLE L

A dye composition was prepared by mixing

| | |
|---|---|
| Dye of Example 50 | 0.300 g |
| Hydroxyethylpropylcellulose | 0.7 g |
| sold as Methocel Hg 400 by Dow Chemical | |
| Monoethanol amine q.s.p. pH 11.4 | |
| Water q.s.p. | 100 cc. |

When this solution was applied to naturally dark brown hair, it imparted violet highlights thereto.

EXAMPLE M

A dye composition was prepared by mixing

| | |
|---|---|
| Dye of Example 51 | 0.400 g |
| Hydroxyethyl propyl cellulose | 0.7 g |
| sold by Dow Chemical as Methocel 65 HG 4000 | |
| Monoethanol amine q.s.p. pH 11.6 | |
| Water q.s.p. | 100 cc. |

When applied to natural brown hair, and rinsed after 15 minutes this dye composition imparted violet highlights to the hair.

EXAMPLE N

A dye composition was prepared by mixing

| | |
|---|---|
| Dye of Example 53 | 1.0 g |
| Butylcellosolve | 8 g |
| Propylene glycol | 8 g |
| Remcopal 334 | 22 g |
| (a polyethoxyether of alkylphenols sold by Gerland) | |
| Remcopal 349 | 22 g |
| (described below) | |
| Ammonia 22° B | 10 cc. |
| Water q.s.p. | 100 cc |

To 20 g of the solution of the above compositions is added 20 g of water oxygented by 20 volumes.

A gel is produced which was applied to hair. 30 minutes after application, the hair is washed, the hair color is light and has mahogany brown overtones.

EXAMPLE O

A hair dye composition is prepared by mixing

| | |
|---|---|
| Dye of Example 55 | 0.035 g |
| Nitroparaphenylenediamine dye | 0.012 g |
| Vinyl acetate-crotonic acid copolymer (90/10) | 1.8 g |
| Vinyl acetate-vinyl pyrrolidone copolymer (40/60) | 0.3 g |
| Ethyl alcohol q.s.p. 50° titer | |
| Triethanolamine pH 7 | |
| Water q.s.p. | 100 cc. |

When applied to naturally light chestnut colored hair, this composition imparted to the hair violet highlights.

EXAMPLE P

A dye composition was prepared by mixing

| | |
|---|---|
| Dye of Example 56 | 0.050 g |
| Vinylacetate-crotonic acid copolymer (90/10) | 1.8 g |
| Vinylacetate-vinylpyrrolidone copolymer (40/60) | 0.3 g |
| Ethyl alcohol 50° titer | |
| Triethanolamine q.s.p. pH 7 | |
| Water q.s.p. | 100 cc. |

When applied to hair dyed a chestnut color, this composition imparted to the hair violet highlights.

EXAMPLES OF COMPOSITIONS

EXAMPLE Q

The dye composition was prepared by mixing:

| | |
|---|---|
| 1'(2'-acetylamino 4'-dimethylamino benzene) 2-azo 1-methyl pyridinium methyl sulfate | 0.02 g |
| 1'-(2-amino 4-hydroxy benzene) 1-azo 4'-hydroxy benzene | 0.02 g |
| Quaternized copolymer of vinylpyrrolidone-dialkyl acrylate amino alkyl of molecular weight of 1,000,000 sold under the name CAFQUAT 755 | 1 g |
| Water, q.s.p. | 100 g |

After washing naturally gray hair containing about 95% white hair, this composition was applied to the gray hair and imparted to the hair gray-rose highlights.

EXAMPLE R

A dye composition was prepared by mixing:

| | |
|---|---|
| 1'-(4'-phenylamino benzene) 2-azo 1,6 dimethyl pyridinium methyl sulfate | 0.01 g |
| 1-anthraquinonylamino propyl trimethyl ammonium methyl sulfate | 0.03 g |
| Quaternized cellulose sold under the trade name JR 400 | 2 g |
| Triethanolamine q.s.p. pH 8 | |
| Water, q.s.p. | 100 g |

After washing hair, the hair was contacted with this composition which is slightly gelled, for a period of time of about 10 minutes. This composition imparted to the hair rose-pearl colored highlights.

EXAMPLE S

A solution was prepared employing the following components:

| | |
|---|---|
| 1'-(4'-amino 8'-hydroxy naphthalene) 2-azo 1-methyl pyridinium methyl sulfate | 0.03 g |
| 1'-(4'-bis(β-hydroxyethyl) amino benzene) 2-azo 1,4-dimethyl pyridinium methyl sulfate | 0.02 g |
| Vinylacetate-crotonic acid copolymer (90/10) | 2 g |
| 2-amino 2-methyl 1-propanol q.s.p. | 100% neutralization |
| Ethyl alcohol q.s.p. | 100 cc |

This alcoholic solution was mixed with a mixture of F.11 trichlorofluoromethane and F.12 the dichlorodifluoromethane for use as an aerosol, wherein the mixture of F.11 and F.12 is in the ratio 60:40, wherein 30 grams of the solution are mixed with 70 grams of propelling agent.

When applied to hair dyed drown, this lacquer imparted to the hair ash-colored highlights.

EXAMPLE T

A solution was prepared by mixing the following ingredients:

| | |
|---|---|
| 1'-(4'-dimethylamino benzene) 2-azo 1-methyl pyridinium methyl sulfate | 0.010 g |
| Vinylacetate-crotonic acid copolymer (90/10) | 2 g |
| 2-amino 2-methyl 1-propanol q.s.p. | 100% neutralization |
| Ethyl alcohol q.s.p. | 100 cc |

This alcoholic solution was mixed with F.11 which is trichlorofluromethane and F.12 which is dichlorodifluoromethane in a ratio 60:40, for use as an aerosol composition, wherein 30 grams of the solution was mixed with 70 grams of the propelling agent.

When applied to hair dyed light brown, this lacquer composition imparted to the hair violet-colored highlights.

EXAMPLE U

A solution was prepared by mixing the following ingredients:

| | |
|---|---|
| 3-methyl 2,3-dihydrobenzothiazole 2:4'-azo 3'-amino 6'-methyl 1'-oxo 1',4'-dihydro benzene | 0.009 g |
| Vinylacetate-crotonic acid copolymer (90/10) | 2 g |
| 2-amino 2-methyl 1-propanol q.s.p. | 100% neutralization |
| Ethyl alcohol q.s.p. | 100 cc |

This alcoholic solution for use as an aerosol was mixed with F.11 which is trichlorofluoromethane and F.12 which is dichlorodifluoromethane in a ratio 60:40, wherein 30 grams of solution were mixed with 70 grams of propelling agent.

When applied to hair dyed blond, this lacquer imparted to the hair very luminous golden highlights.

EXAMPLE V

A solution was prepared by mixing the following ingredients:

| | |
|---|---|
| 1'-(2'-nitro 4'-dimethylamino benzene) 2-azo) 1-methyl pyridinium methyl sulfate | 0.5 g |
| Ethanol | 40 g |
| Polyvinylpyrrolidone-vinylacetate copolymer (30/70) | 1.5 g |
| The chloride of zinc and of N-[(N'M'ethyl-acetylamino ethyl) 4'-amino]phenyl 2-azo 3-amino benzoquinone diimine | 0.1 g |
| Triethanolamine q.s.p. pH 7 | |
| Water, q.s.p. | 100 g |

This composition was applied as a solution to naturally gray hair which was 95% white. The solution imparted to the hair a violet-red highlight.

EXAMPLE W

A solution was prepared by mixing the following ingredients:

| | |
|---|---|
| 1'-(4'-amino 3'-methoxy benzene) 2-azo 1-methyl pyridinium methyl sulfate | 0.02 g |
| Ethanol | 50 g |
| Mono-butyl ester of the copolymer methyl vinylether-maleic anhydride sold under the trade name GANTREZ ES 415 | 2 g |
| 1,4-(morpholino ethyl) diamino anthraquinone | 0.2 g |
| Triethanolamine q.s.p. pH 8 | |
| Water q.s.p. | 100 g |

This composition was applied, as a lotion, to hair which had been stripped. The composition imparted to the hair mauve overtones.

EXAMPLE X

A solution was prepared by mixing the following ingredients:

| | |
|---|---|
| 1'-(2',4'-diamino 5'-methyl benzene) 2-azo 1,5-dimethyl pyridinium methyl sulfate | 0.04 g |
| Ethanol | 70 g |
| Polyvinylpyrrolidone K/30 | 3 g |
| Methyl [(1-anthraquinonylamino propyl) trimethyl-ammonium] sulfate | 0.5 g |
| Triethanolamine q.s.p. pH 6.5 | |
| Water q.s.p. | 100 g |

When this composition, used as a lotion, was applied to naturally white hair, the composition imparted to the hair a rose salmon tint.

EXAMPLE Y

A solution was prepared by mixing the following ingredients:

| | |
|---|---|
| 1'-(4'-dimethylamino benzene) 2-azo 1,5-dimethyl pyridinium methylsulfate | 0.3 |
| Ethanol | 60 |
| Polyvinylpyrrolidone-vinylacetate copolymer (30/70) | 2.5 |
| 1'-(2-amino 4-hydroxy benzene) 1-azo 4'hydroxy benzene | 0.4 |
| Triethanolamine q.s.p. pH 6 | |
| Water q.s.p. | 10 |

This composition, when applied to gray hair, as a lotion, imparted to the hair copper-colored highlights.

This composition, when applied to gray hair, as a lotion, imparted to the hair copper-colored highlights.

The molecular weight of the vinylacetate-crotonic acid copolymers 30/70 used in examples A-Y is 50,000.

The polyvinylpyrrolidone-vinylacetate copolymer used in examples A-Y have a molecular weight of 160,000 for copolymer 30/70, and a viscosity of 3,3 to 4 in a 5% ethanolic solution for copolymer vinyl-acetate-polyvinylpyrrolidone (40/60).

The polyvinylpyrrolidone K 30 has a molecular weight of 40,000.

What is claimed is:

1. A diazamerocyanine, including the mesomeric forms thereof, having the formula

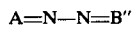

wherein A is of the formula

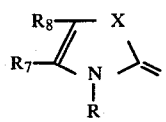

wherein:
R is selected from the group consisting of lower alkyl having 1-4 carbon atoms and phenyl;
X is selected from the group consisting of oxygen; sulfur; —NR'—, wherein R' is lower alkyl having 1-4 carbon atoms; —CR'$_9$=CR'$_{10}$ wherein R'$_9$ is hydrogen, alkyl of 1 to 4 carbon atoms or cyano and wherein R'$_{10}$ is hydrogen or alkyl of 1 to 4 carbon atoms;

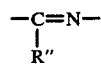

wherein R" is selected from the group consisting of hydrogen and lower alkyl having 1-4 carbon atoms; and —C(R")(R")—, wherein R" each independently have the meaning given above;
R$_7$ is selected from the group consisting of hydrogen, lower alkyl having 1-4 carbon atoms, cyano and phenyl;
R$_8$ is selected from the group consisting of hydrogen, halogen and lower alkyl having 1-4 carbon atoms, provided that R$_7$ and R$_8$, when taken together with the carbon atoms to which they are linked, form a benzene ring or a benzene ring substituted by halo, a lower alkyl having 1-4 carbon atoms, lower alkoxy having 1-4 carbon atoms or nitro; and B" is

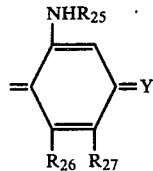

wherein:
Y represents a member selected from the group consisting of

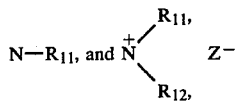

wherein R$_{11}$, and R$_{12}$, each independently represent a member selected from the group consisting of hydrogen and lower alkyl having 1-4 carbon atoms, and z⁻ halide, perchlorate, fluoroborate, acetate, bisulfate or sulfate;

R$_{25}$ represents a member selected from the group consisting of hydrogen and

wherein W represents a member selected from the group consisting of oxygen and sulfur, and R' represents a member selected from the group consisting of amino and lower alkyl having 1-4 carbon atoms; and R$_{26}$ and R$_{27}$ each independently represent a member selected from the group consisting of hydrogen, lower alkyl having 1-4 carbon atoms and methoxy; provided that R$_{27}$ represents hydrogen when R$_{11}$, and R'$_{12}$ and R$_{25}$ represent hydrogen.

2. A diazamerocyanine, including the mesomeric forms thereof, having the formula

wherein A is of the formula

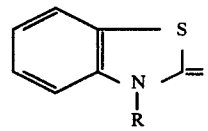

wherein:
R is selected from the group consisting of lower alkyl having 1-4 carbon atoms and phenyl; and B" is

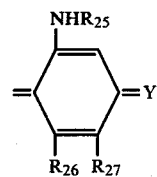

wherein:
Y represents a member selected from the group consisting of

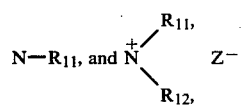

wherein R$_{11}$, and R$_{12}$, each independently represent a member selected from the group consisting of hydrogen and lower alkyl having 1-4 carbon atoms, and Z⁻ is halide, perchlorate, fluoroborate, acetate, bisulfate or sulfate;

R$_{25}$ represents a member selected from the group consisting of hydrogen and

wherein W represents a member selected from the group consisting of oxygen and sulfur, and R' represents a member selected from the group consisting of amino and lower alkyl having 1–4 carbon atoms; and $R_{26}$ and $R_{27}$ each independently represent a member selected from the group consisting of hydrogen, lower alkyl having 1–4 carbon atoms and methoxy; provided that $R_{27}$ represents hydrogen when $R'_{11}$, and $R'_{12}$ and $R_{25}$ represent hydrogen.

3. 2[(1,3-diamino 6-methyl-phenyl(4)azo]-3 methyl benzothiazolium perchlorate.

* * * * *